(12) United States Patent
Yamaguchi et al.

(10) Patent No.: US 7,279,298 B2
(45) Date of Patent: Oct. 9, 2007

(54) PROTEIN-DEAMIDATING ENZYME, GENE ENCODING THE SAME, PRODUCTION PROCESS THEREFOR, AND USE THEREOF

(75) Inventors: Shotaro Yamaguchi, Norwich (GB); Akira Matsuura, Aichi (JP)

(73) Assignee: Amano Pharmaceutical Co., Ltd., Nagoya-shi (JP)

( * ) Notice: Subject to any disclaimer, the term of this patent is extended or adjusted under 35 U.S.C. 154(b) by 440 days.

(21) Appl. No.: 10/815,751

(22) Filed: Apr. 2, 2004

(65) Prior Publication Data

US 2004/0166558 A1 Aug. 26, 2004

Related U.S. Application Data

(62) Division of application No. 09/793,495, filed on Feb. 27, 2001, now Pat. No. 6,770,469, which is a division of application No. 09/324,910, filed on Jun. 3, 1999, now Pat. No. 6,251,651.

(30) Foreign Application Priority Data

Jun. 4, 1998 (JP) ................... 10-173940

(51) Int. Cl.
*C12Q 1/00* (2006.01)
*C12Q 1/48* (2006.01)

(52) U.S. Cl. ............ 435/15; 435/4; 435/6; 435/69.1; 435/183; 435/200; 435/211; 536/23.2

(58) Field of Classification Search ........... 435/4, 435/69.1, 183, 200, 219, 220, 252–3, 320–1; 536/23–2; 530/350
See application file for complete search history.

(56) References Cited

U.S. PATENT DOCUMENTS 3,796,633 A 3/1974 Kikuhi et al.

5,082,672 A 1/1992 Hamada et al.
5,279,839 A * 1/1994 Gottmann et al. ............ 426/20

FOREIGN PATENT DOCUMENTS

EP 0 976 829 A2 2/2000
WO WO97 43910 A 11/1997

OTHER PUBLICATIONS

J.S. Hamada, et al., "Preparation and Functional Properties of Enzymatically Deamidated Soy Proteins", *Journal of Food Science.*, vol. 54, No. 3, May 1989—Hybe 1989 (Jun. 1989), pp. 598-601, 635.
I.A. Vaintraub, et al., "Protein Deamidase from Germinating Wheat Grains", *FEBS Letters,* vol. 302, No. 2, May 11, 1992, pp. 169-171.
Yamaguchi, et al., "A Novel Protein-Deamidating Enzyme from *Chryseobacterium proteolyticum* SP SP. Nov. , a Newly Isolated Bacterium from Soil", *Appl. Environ, Microbiol.,* vol. 66, No. 8, Aug. 2000, pp. 3337-3343. (XP-002162600).
DATABASE WPI, Section Ch, Week 199922, Derwent Publications Ltd., London, GB; Class B04, AN 1999-257687, XP002162641 & JP 11 075835 (Amano Pharm KK), Mar. 23, 1999.

* cited by examiner

*Primary Examiner*—Manjunath Rao
(74) *Attorney, Agent, or Firm*—Edwards Angell Palmer & Dodge LLP

(57) ABSTRACT

A novel enzyme which has an activity to release side chain carboxyl groups and ammonia from a protein by acting upon side chain amido groups in the protein. This invention relates to a method for the production of an enzyme, which comprises culturing in a medium a strain that belongs to a bacterium classified into *Cytophagales* or *Actinomycetes* and has the ability to produce an enzyme having a property to deamidate amido groups in protein, thereby effecting production of said enzyme, and subsequently collecting said enzyme from the culture mixture. It also relates to a method for the modification of protein making use of a novel enzyme which directly acts upon amido groups in protein as well as to an enzyme which has a property to deamidate amido groups in protein and a gene which encodes said enzyme.

9 Claims, 18 Drawing Sheets

PROTEIN-DEAMIDATING ENZYME, GENE ENCODING THE SAME, PRODUCTION PROCESS THEREFOR, AND USE THEREOF

This application is a Divisional Application of the prior application No. 09/793,495 (U.S. Pat. No. 6,770,469) filed Feb. 27, 2000, which is a Divisional Application of the prior application No. 09/324,910 (U.S. Pat. No. 6,251,651) filed Jun. 3, 1999.

FIELD OF THE INVENTION

This invention relates to a novel enzyme, namely a novel enzyme which acts upon side chain amido groups in protein and thereby releases side chain carboxyl groups and ammonia, and to a production method thereof. More particularly, it relates to a method for the production of an enzyme having a property to deamidate amido groups in protein, which comprises culturing a bacterial strain capable of producing an enzyme having a property to deamidate amido groups in protein, that belongs to *Cytophagales* or *Actinomycetes*, more particularly to the genus *Chryseobacterium, Flavobacterium, Empedobacter, Sphingobacterium, Aureobacterium* or *Myroides*, in a medium, thereby allowing the strain to produce said enzyme, and subsequently collecting said enzyme from the culture mixture. This invention also relates to a method for the modification of protein, which uses a novel enzyme having a property to directly act upon amido groups in protein. It also relates to an enzyme which has a property to deamidate amido groups in protein, to a gene which encodes said enzyme, to a vector which contains said gene, to a transformant transformed with said vector, and to a method for the production of an enzyme having a property to deamidate amido groups in protein, which comprises culturing said transformant in a medium, thereby allowing the transformant to produce said enzyme, and subsequently collecting said enzyme from the culture mixture.

BACKGROUND ART

Glutaminase/asparaginase are enzymes which hydrolyze glutamine/asparagine to convert them into glutamic acid/aspartic acid and ammonia, and it is well known that these enzymes are obtained from animals, plants and microorganisms. However, these enzymes specifically act on free glutamine/asparagine and cannot deamidate glutamine/asparagine in peptides or polypeptides.

Also, transglutaminase is known as an enzyme which acts upon amido groups existing in a peptide state. Transglutaminase catalyzes the reaction of introducing an amine compound into protein by covalent bonding or the reaction of cross-linking the glutamine residue and lysin residue of protein via $\epsilon$-($\gamma$-glutamyl)lysine-isopeptide bonding, in which the amido group of peptide bonded glutamine as an acyl donor and the amino group of the primary amine as an acyl acceptor. It is known that, when amine or lysin does not exits in the reaction system or blocked, water acts as an acyl acceptor and the glutamine residue in paptide is deamidated to become glutamic acid residue. As described above, transglutaminase is basically an acyl group transferase. Accordingly, when allowed to act on a usual protein, this enzyme causes cross-linking of protein and does not deamidate the protein. Accordingly, transglutaminase is different from the enzyme of the present invention.

In addition, Peptideglutaminase I and Peptideglutaminae II produced by *Bacillus circulans* are known as an enzyme which performs deamidation by acting upon glutamine bonded in peptide. It is known that the former acts on the glutamine residue existing at the C terminal of peptide and the latter acts on the glutamine residue existing in the peptide. However, these enzymes hardly acts upon a high molecular weight protein and acts only upon a low molecular weight peptide [M. Kikuchi, H. Hayashida, E. Nakano and K. Sakaguchi, *Biochemistry*, vol. 10, 1222-1229 (1971)].

Also, plural studies have been made to attempt to allow these enzyme (Peptideglutaminase I and II) to act upon a high molecular weight protein rather than a low molecular weight peptide. As a result, it has been revealed that these enzymes do not substantially act on a high molecular weight protein but act only on a protein hydrolysate peptide. Gill et al. reported that each of Peptideglutaminase I and II does not act on milk casein and whey protein both in native form and denatured form. They also reported that, as a result of studies on activities on protein hydrolysate, only Peptideglutaminase II acted only on peptide having a molecular weight of 5000 or less (B. P. Gill, A. J. O'Shaughnessey, P. Henderson and D. R. Headon, Ir. *J. Food Sci. Technol.*, vol. 9, 33-41 (1985)). Similar studies were carried out by Hamada et al. using soy bean protein and the result was consistent with the result by Gill et al. That is, it was reported that these enzymes showed deamidation percentage of 24.4% to 47.7% on soy bean peptide (Peptone), but did not substantially act on soy bean protein (0.4% to 0.8%) (J. S. Hamada, F. F. Shih, A. W. Frank and W. E. Marshall, J. Food *Science*, vol. 53, no. 2, 671-672 (1988)).

There is an report suggesting existence of an enzyme originating from plant seed, which catalyzes deamidation of protein (cf. I. A. Vaintraub, L. V. Kotova, R. Shara, *FEBS Letter*, Vol. 302, 169-171 (1992)). Although this report observed ammonia release from protein using a partially purified enzyme sample, it is clear that this report does not prove existence of an enzyme of the present invention from the following reasons. In this report, a partially purified enzyme sample was used, inexistence of protease activity was not confirmed, and no change in molecular weight of substrate protein after the reaction was not confirmed. Accordingly, this report does not exclude the possibility that plural enzymes (not one enzyme) such as protease, peptidase, etc. acted on protein to release glutamine/asparagine as free amino acids and ammonia was released by glutaminase/asparaginase which deamidate these free amino acids. Similarly, there is a possibility that glutamine-containing low molecular weight peptide produced in a similar way is deamidated by peptideglutaminase-like enzyme. In addition, there is a possibility that deamidation occurred as a side-reaction by protease. In particular, it should be noted that this report clearly describes that the partially purified preparation had glutaminase activity which acted on free glutamine to release ammonia.

Accordingly, there is no report until now which confirmed existence of an enzyme which can catalyzes deamidation of on high molecular weight protein by purification of the enzyme as a single protein and isolation and expression of the gene encoding the same.

In general, when carboxyl groups are formed by deamidation of glutamine and asparagine residues in protein, negative charge of the protein increases and, as the results, its isoelectric point decreases and its hydration ability increases. It also causes reduction of mutual reaction between protein molecules, namely, reduction of association ability, due to the increment of electrostatic repulsion. Solubility and water dispersibility of protein sharply increases by these changes. Also, the increment of negative charge of protein results in the change of the higher-order structure of the protein caused by loosening of its folding, thus exposing the hydrophobic region buried in the protein molecule to the molecular surface. In consequence, a deamidated protein has amphipathic property and becomes an ideal surface active agent, so that emulsification ability, emulsification stability, foamability and foam stability of the protein are sharply improved.

Thus, deamidation of a protein results in the improvement of its various functional characteristics, so that the use of the protein increases sharply (for example, see *Molecular Approaches to Improving Food Quality and Safety*, D. Chatnagar and T. E. Cleveland, eds., Van Nostrand Reinhold, New York, 1992, p. 37).

Accordingly, a large number of methods for the deamidation of protein have been studied and proposed. An example of chemical deamidation of protein is a method in which protein is treated with a mild acid or a mild alkali under high temperature condition. In general, amido groups of glutamine and asparagine residues in protein are hydrolyzed by an acid or a base. However, this reaction is non-specific and accompanies cutting of peptide bond under a strong acid or alkali condition. It also accompanies denaturation of protein to spoil functionality of the protein.

Accordingly, various means have been devised with the aim of limiting these undesired reactions, and a mild acid treatment (for example, see J. W. Finley, *J. Food Sci.*, 40, 1283, 1975; C. W. Wu, S. Nakai and W. D. Powie, *J. Agric. Food Chem.*, 24, 504, 1976) and a mild alkali treatment (for example, see A. Dilollo, I. Alli, C. Biloarders and N. Barthakur, *J. Agric. Food Chem.*, 41, 24, 1993) have been proposed. In addition, the use of sodium dodecyl sulfate as an acid (F. F. Shih and A. Kalmar, *J. Agric. Food Chem.*, 35, 672, 1987) or cation exchange resin as a catalyst (F. F. Shih, *J. Food Sci.*, 52, 1529, 1987) and a high temperature treatment under a low moisture condition (J. Zhang, T. C. Lee and C. T. Ho, *J. Agric. Food Chem.*, 41, 1840, 1993) have also been attempted.

However, all of these methods have a difficulty in completely restricting cutting of peptide bond. The cutting of peptide bond is not desirable, because it inhibits functional improvement of protein expected by its deamidation and also causes generation of bitterness. Also, the alkali treatment method is efficient in comparison with the acid treatment method, but it has disadvantages in that it causes racemization of amino acids and formation of lysinoalanine which has a possibility of exerting toxicity.

On the other hand, some enzymatic deamidation methods have also been attempted with the aim of resolving the aforementioned problems of the chemical methods. Namely, a protease treatment method under a high pH (pH 10) condition (A. Kato, A. Tanaka, N. Matsudomi and K. Kobayashi, *J. Agric. Food Chem.*, 35, 224, 1987), a transglutaminase method (M. Motoki, K. Seguro, A. Nio and K. Takinami, *Agric. Biol. Chem.*, 50, 3025, 1986) and a peptideglutaminase method (J. S. Hamada and W. E. Marshall, *J. Food Sci.*, 54, 598, 1989) have been proposed, but each of these methods has disadvantages.

Firstly, the protease method cannot avoid cutting of peptide bond as its original reaction. As described in the foregoing, cutting of peptide bond is nor desirable.

In the case of the transglutaminase method, it is necessary to chemically protect ε-amino group of lysine residue in advance, in order to prevent cross-linking reaction caused by the formation of isopeptide bond between glutamine and lysine, as the original reaction of the enzyme. When a deamidated protein is used in food, it is necessary to deamidate glutamine after protection of the ε-amino group with a reversible protecting group such as citraconyl group, to remove the protecting group thereafter and then to separate the deamidated protein from the released citraconic acid. It is evident that these steps sharply increase the production cost and are far from the realization.

In the case of the peptideglutaminase method, on the other hand, it is necessary to use a protein hydrolysate, because this enzyme hardly reacts upon protein but acts only upon a low molecular weight peptide and cannot therefore be applied to raw protein.

In consequence, though the reaction selectivity due to high substrate specificity of enzymes is originally one of the greatest advantages of the enzymatic method, which surpasses chemical and physical methods, it is the present situation that the enzymatic method cannot be put into practical use for the purpose of effecting deamidation of protein because of the absence of an enzyme which does not generate side reactions and is suited for the deamidation of high molecular weight protein.

Thus, though the deamidation of protein is an excellent modification method which will result in the great functional improvement, both of the conventional chemical and enzymatic methods have disadvantages, and their realization therefore is not completed yet.

SUMMARY OF THE INVENTION

In view of the above, the inventors of the present invention have conducted extensive studies on the screening of an inexpensive microorganism to be used as the source of an enzyme capable of directly acting upon amido groups which are bonded to protein and thereby effecting deamidation of the protein and, as a result, found that a new strain belonging to the genus Chryseobacterium, newly isolated from a soil sample by the present inventors, can produce an enzyme which exerts the deamidation function by directly acting upon amido groups in the bonded state in protein without accompanying cutting of peptid bonding and cross-linking of protein molecules. The present invention has been accomplished on the basis of this finding. In this specification, an enzyme which has the aforementioned actions is called a "protein-deamidating enzyme".

Thereafter, the present inventors have selected strains belonging to the genus *Chryseobacterium* randomly from type cultures and examined their ability to produce the protein-deamidating enzyme. As the results, the productivity of this enzyme was found in all of the selected strains, as well as in other strains which belong, for example, to the genera *Flavobacterium*, *Empedobacter*, *Sphingobacterium*, *Aureobacterium* and *Myroides*. Each of these strains is a bacterium classified into *Cytophagales* or *Actinomycetes*, and the bacteria belong to the genus *Chryseobacterium*, *Empedobacter*, *Flavobacterium*, and *Myroides* are classified into *Flavobacteriaceae*.

The present inventors have then isolated and purified the protein-deamidating enzyme, determined nucleotide sequence of the gene coding for said protein-deamidating enzyme and confirmed that the protein-deamidating enzyme can be produced using a transformant transformed with a vector containing said gene.

Accordingly, the present invention relates to a method for the production of a protein-deamidating enzyme using a microorganism capable of producing the protein-deamidating enzyme, a method for the modification of protein using the protein-deamidating enzyme, a composition for use in the modification of protein, which comprises the protein-deamidating enzyme as the active ingredient, a method for the improvement of functionality of protein using the protein-deamidating enzyme, a method for the improvement of functionality of food using the protein-deamidating enzyme, a method for the improvement of extraction efficiency of protein and/or peptide using the protein-deamidating enzyme and a method for the control of transglutaminase reaction using the protein-deamidating enzyme.

The present invention also relates to a protein-deamidating enzyme, a gene which encodes said enzyme, a vector which contains said gene, a transformant transformed with said vector and a method for the production of the protein-deamidating enzyme, which comprises culturing said transformant in a medium, thereby allowing the transformant to produce the protein-deamidating enzyme, and subsequently collecting the protein-deamidating enzyme from the culture mixture, and the like.

DETAILED DESCRIPTION OF THE INVENTION

Figure 1:
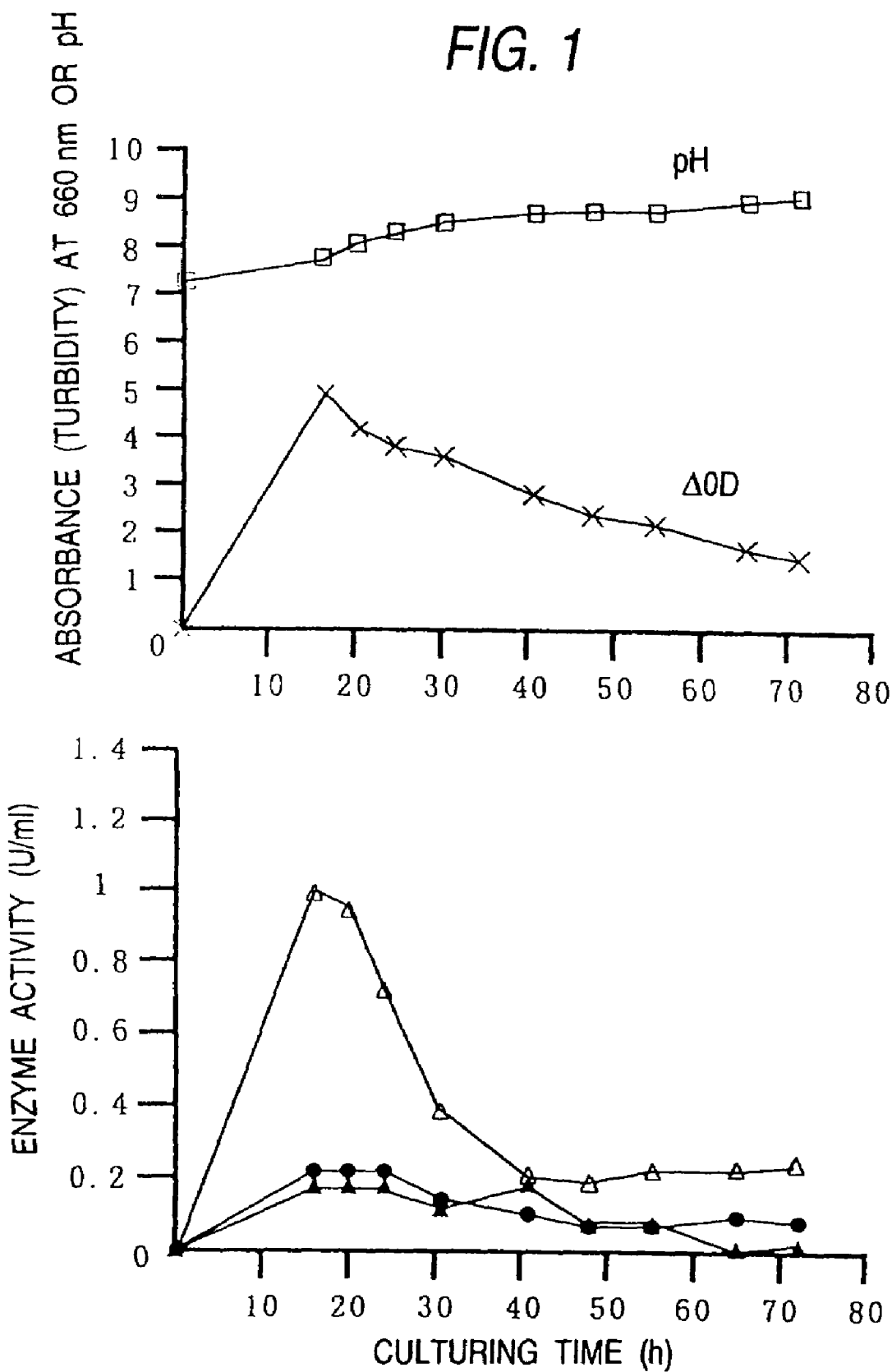
FIG. 1 is a graph showing time course of the culturing of *Chryseobacterium gleum* JCM 2410 in lactose medium, in which the open square indicates changes in pH, the cross indicates changes in the absorbance of culture medium at 660 nm, the open triangle indicates changes in the protease activity when casein is used as the substrate, the closed circle indicates changes in the protein-deamidating enzyme activity when Z-Gln-Gly is used as the substrate and closed triangle indicates changes in the protein-deamidating enzyme activity when casein is used as the substrate.

The protein-deamidating enzyme of the present invention acts on the amido group of asparagine residue or glutamine residue in proteins but the moiety on which this enzyme acts is not particularly limited. For example, the protein-deamidating enzyme of the present invention can be effective on the amido group connected to other amino acids. The term "protein" as used herein is not limited to simple protein but also includes protein complexes, conjugated proteins with saccharides, lipids, etc., and the like. The molecular weight of the protein is not particularly limited and generally in the range of from 5000 or more and preferably in the range of from 10,000 to 2,000,000.

The protein-deamidating enzyme of the present invention can be used also for deamidation of peptides having an amido group, derivatives thereof, and the like. Examples of the peptides include those having amino acid residues of 2 to 50. Peptides used as nutrition-improving agents are preferable.

Thus, the protein-deamidating enzyme of the present invention can act on substrates from dipeptides to high molecular weight proteins, including polypeptides. Incidentally, the term "polypeptides" as used in this specification includes proteins.

A microorganism capable of producing the protein-deamidating enzyme of the present invention can be screened, for example, in the following manner. That is, an enrichment culturing is carried out by inoculating a soil suspension into an isolation liquid medium containing Z-Gln-Gly as the sole nitrogen source, the culture broth is spread and cultured on an isolation plate agar medium having the same composition, and then colonies grown on the medium are selected and picked up. A strain having the ability to release ammonia from Z-Gln-Gly can be selected by culturing these colonies in an appropriate liquid medium.

A microorganism capable of producing the protein-deamidating enzyme can be screened from the thus selected strains using casein as the substrate and ammonia-releasing activity as an index.

A strain screened in this manner was identified as a species belonging to the genus *Chryseobacteriumn* in accordance with Bergey's Manual of *Determinative Bacteriology*. In addition, it was confirmed by the aforementioned testing method that strains selected at random from type cultures of the genus *Chryseobacterium* can produce the protein-deamidating enzyme. Illustrative examples of such strains include *Chryseobacterium gleum* JCM 2410, *Chryseobacterium indologenes* IFO 14944, *Chryseobacterium meningosepticum* IFO 12535, *Chryseobacterium balustinum* IFO 15053, *Chryseobacterium indoltheticum* ATCC 27950, and *Chryseobacterium scophthalnum* CCM4109.

When other microorganisms are subjected to the same screening method, production of the protein-deamidating enzyme was confirmed in strains belonging to the genus *Flavobacterium*, more illustratively *Flavobacterium aquatile* IFO 15052, the genus *Empedobacter*, more illustratively *Empedobacter brevis* IFO 14943, the genus *Sphingobacterium*, more illustratively *Sphingobacterium spiritivorum* IFO 14948 and *Sphingobacterium heparinum* IFO 12017, the genus *Aureobacterium*, more illustratively *Aureobacterium esteraromatidum* IFO 3751 and the genus *Myroides*, more illustratively *Myroides odoratus* IFO 14945.

In this connection, this enzyme can be distinguished from known transglutaminase, because it does not have the activity to catalyze formation of isopeptide between glutamine residue and lysine residue in protein, namely transglutaminase activity. It can also be distinguished from known protease, because it does not have the activity to hydrolyze peptide bond of protein, namely protease activity.

Regarding the culturing method of each of the aforementioned strains for the production of the protein-deamidating enzyme, either a liquid culturing or a solid culturing, but preferably a liquid culturing, may be used. For example, the liquid culturing can be carried out in the following manner.

Any medium can be used with the proviso that a microorganism capable of producing the protein-deamidating enzyme can grow in the medium. Examples of the medium to be used include those which contain carbon sources such as glucose, sucrose, glycerol, dextrin, molasses and organic acids, nitrogen sources such as ammonium sulfate, ammonium carbonate, ammonium phosphate, ammonium acetate, peptone, yeast extract, corn steep liquor, casein hydrolysate and beef extract and inorganic salts such as potassium salts, magnesium salts, sodium salts, phosphoric acid salts, manganese salts, iron salts and zinc salts.

The medium pH is adjusted to a value of approximately from 3 to 10, preferably from about 7 to 8, and the culturing is carried out under aerobic conditions at a temperature of generally from about 10 to 50° C., preferably from about 20 to 37° C., for a period of from 1 to 20 days, preferably from 3 to 12 days. As the culturing method, a shaking culture method or an aerobic submerged jar fermentor culture method may be used.

The protein-deamidating enzyme of the present invention can be obtained by isolating the protein-deamidating enzyme from the thus obtained culture broth in the usual way. For example, when the protein-deamidating enzyme is isolated and purified from the culture broth, purified protein-deamidating enzyme can be obtained by treating it in the usual way by the combination of centrifugation, UF concentration, salting out and various types of chromatography such as of an ion exchange resin.

The present invention is described more illustratively. That is, the aforementioned *Chryseobacterium gleum* JCM 2410 was used as a protein-deamidating enzyme producing strain and cultured in a liquid medium, and production, purification and properties of the enzyme were examined.

One loopful of cells grown on a fresh slant medium were inoculated into the following lactose medium and cultured on a shaker at 30° C. for 2 to 7 days, and then centrifugation supernatant is obtained. Lactose medium composition (pH 7.2)

| | |
|---|---|
| Lactose (manufactured by Wako Pure Chemical Industries) | 0.5% |
| Polypeptone (manufactured by Wako Pure Chemical Industries) | 1.0% |
| $Na_2HPO_4.H_2O$ | 0.17% |
| $KH_2PO_4$ | 0.025% |
| $MgSO_4.7H_2O$ | 0.025% |
| $FeSO_4.7H_2O$ | 0.005% |

Time course of the culturing is shown in FIG. 1.

After completion of the culturing, the enzyme of interest was purified by subjecting the culture broth to centrifugation (12,000 rpm, 4° C., 20 minutes) to obtain the supernatant as a crude enzyme solution, and treating the thus obtained solution by UF concentration (SEP-0013), salting out, Phenyl-Sepharose and Sephacyl S-100. Steps of the purification are shown in Table 1.

TABLE 1

| | Total protein mg | Total activity U | Specific activity U/mg | Recovery Yield % |
|---|---|---|---|---|
| Culture broth | 83.50 | 16.53 | 0.198 | 100 |
| UF concentration | 11.78 | 13.17 | 1.12 | 79.7 |
| Salting out | 4.10 | 10.03 | 4.09 | 60.7 |
| Phenyl-Sepharose | 0.187 | 3.10 | 16.6 | 18.7 |
| Sephacyl S-100 | 0.073 | 2.26 | 31.1 | 13.7 |

In this connection, measurement of the enzyme activity was carried out in the following manner using Z-Gln-Gly and casein as substrates.

Activity measuring method: A 10 μl portion of each enzyme solution is added to 100 μl of 176 mM phosphate buffer (pH 6.5) containing 10 mM Z-Gln-Gly and incubated at 37° C. for 60 minutes, and then the reaction is stopped by adding 100 μl of 12% trichloroacetic acid solution. After centrifugation (15,000 rpm, 4° C., 5 minutes), the resulting supernatant is measured in the following manner using F-kit ammonia (manufactured by Boehringer-Mannheim) (A1). Separately, the same measurement is carried out using water instead of the enzyme solution (A2).

F-Kit Ammonia

A 10 μl portion of the supernatant and 190 μl of water are added to 100 μl of Reagent 2, the resulting mixture is allowed to stand at room temperature for 5 minutes and then the absorbance of 100 μl portion of the reaction solution is measured at 340 nm (E1). The remaining 200 μl portion is mixed with 1.0 μl of Reagent 3 (glutamate dehydrogenase), allowed to stand at room temperature for 20 minutes and then the absorbance of the remaining 200 μl is measured at 340 nm (E2).

The amount of enzyme which releases 1 μmol of ammonia within one minute under the above reaction conditions is defined as one unit and calculated based on the following formula.

$$U/ml = 1.76 \times [A1(E1-E2) - A2(E1-E2)]$$

Using 1% casein (Hermastein, manufactured by Merck) instead of 10 mM Z-Gln-Gly as the substrate, the activity is measured in the same manner to confirm that the enzyme acts upon amino groups bonded to the protein. In this case, the protease activity was also checked by measuring the absorbance of the centrifugation supernatant after termination of the reaction at 280 nm. The amount of enzyme which increases 10 D units under this condition was defined as one unit of protease activity.

In addition, glutaminase activity was measured by the similar method except that 10 mM glutamine was used as the substrate instead of 10 mM Z-Gln-Gly.

Transglutaminase activity was measured by the following hydroxamic acid method using Z-Gln-Gly as the substrate.

| Reagent A | 0.2 M Tris-HCl buffer (pH 6.0) |
| | 0.1 M hydroxylamine |
| | 0.01 M reduced glutathione |
| | 0.03 M benzyloxycarbonyl-L-glutaminylglycine |
| Reagent B | 3 N hydrochloric acid |
| | 12% trichloroacetic acid |
| | 5% FeCl$_3$·6H$_2$O (dissolved in 0.1 M HCl) |

A 1:1:1 mixture of these solutions is used as reagent B.

A 0.05 ml portion of each enzyme solution is mixed with 0.5 ml of the reagent A to carry out 10 minutes of the reaction at 37° C., the reaction solution is mixed with 0.5 ml of the reagent B to stop the reaction and to effect formation of Fe complex, and then the absorbance at 525 nm is measured. As a control, the same reaction is carried out using the same enzyme solution heat-inactivated in advance, and the absorbance is measured to calculate its difference from the absorbance of the intact enzyme solution. Separately from this, a calibration curve is prepared using L-glutamic acid γ-monohydroxamate instead of the enzyme solution, for use in the calculation of the amount of formed hydroxamic acid based on the just described difference in absorbance, and the enzyme activity which forms 1 μmol of hydroxamic acid within one minute is defined as one unit.

In this connection, the amount of protein was determined using BCA Protein Assay Kit (manufactured by Pierce) and bovine serum albumin as the standard protein.

(1) Measurement of molecular weight: 20 kDa as determined by SDS-polyacrylamide gel electrophoresis.

Figure 2:
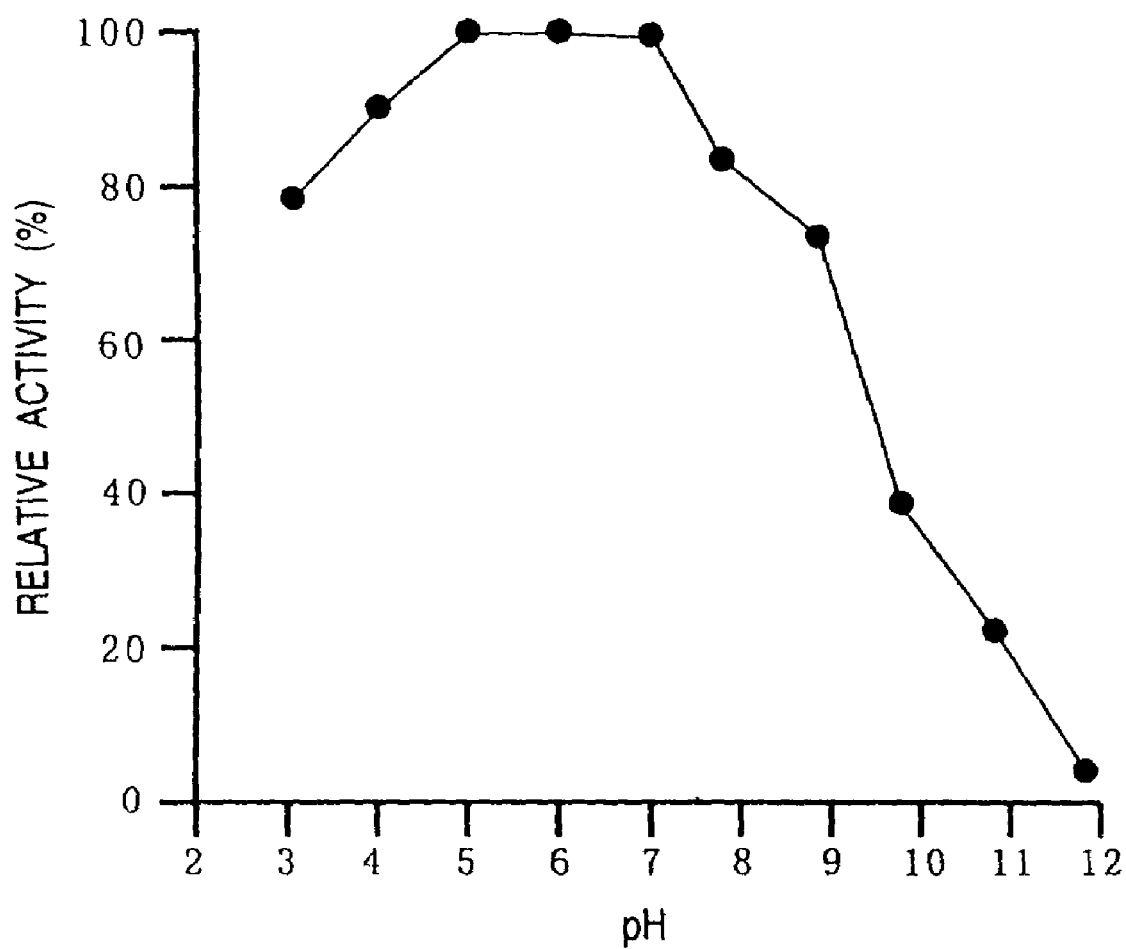
FIG. 2 is a graph showing optimum pH of the protein-deamidating enzyme obtained from *Chryseobacterium gleum* JCM 2410.

(2) Measurement of optimum pH: A 100 μl portion of 40 mM Britton-Robinson buffer solution (having a pH value of from 3 to 12) containing 10 mM Z-Gln-Gly was pre-incubated at 37° C. for 5 minutes, 10 μl of each enzyme solution containing 0.32 μg of the protein-deamidating enzyme was added to the buffer and incubated at 37° C. for 60 minutes to measure the enzyme activity. The results are shown in FIG. 2.

Figure 3:
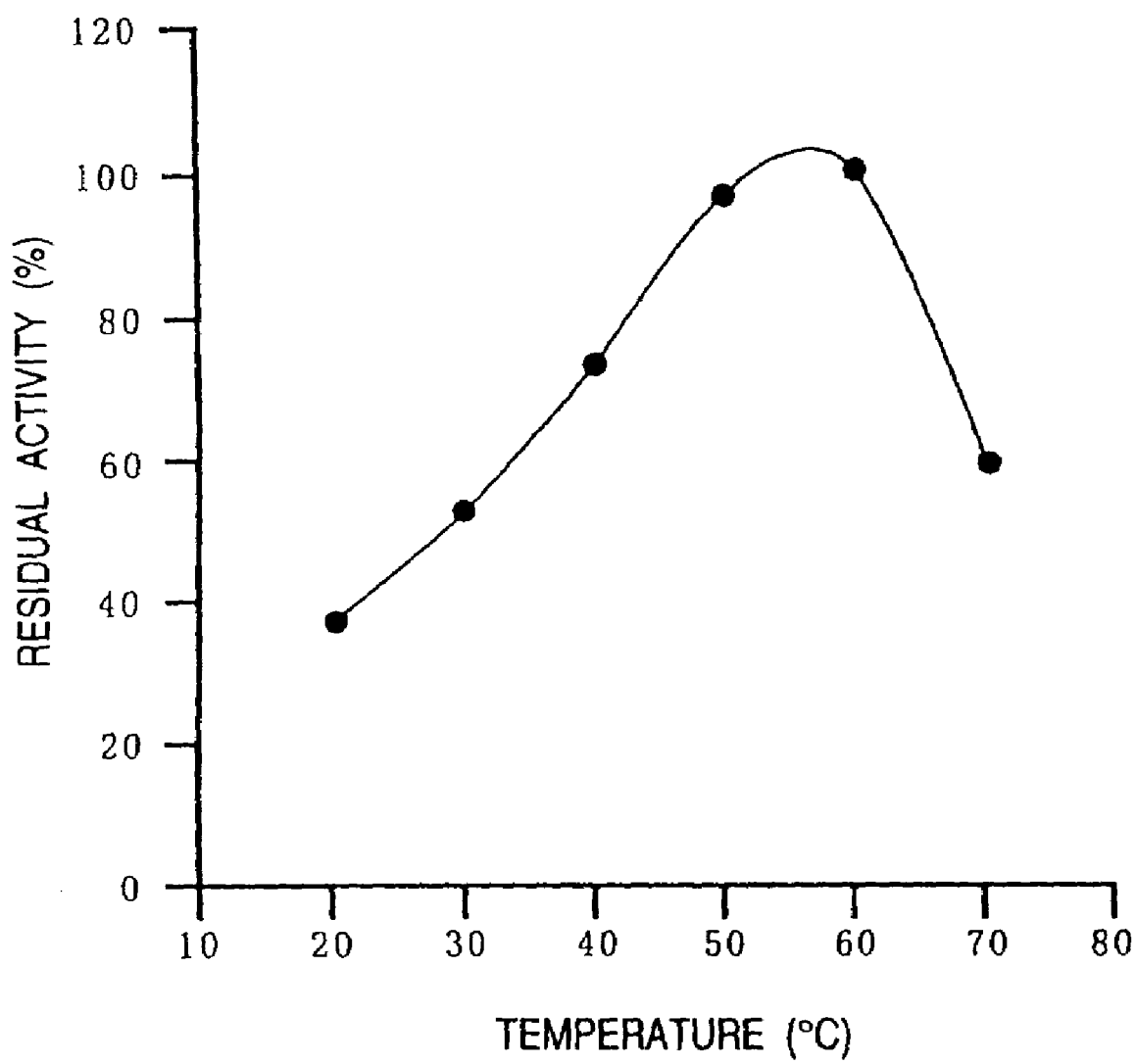
FIG. 3 is a graph showing optimum temperature of the protein-deamidating enzyme obtained from *Chryseobacterium gleum* JCM 2410.

(3) Measurement of optimum temperature: A 10 μl portion of enzyme solution containing 1.21 μg of the protein-deamidating enzyme was added to 100 μl of a substrate solution [176 mM phosphate buffer (pH 6.5) containing 10 mM Z-Gln-Gly], and the reaction was carried out at each temperature for 60 minutes to measure the enzyme activity. The results are shown in FIG. 3.

Figure 4:
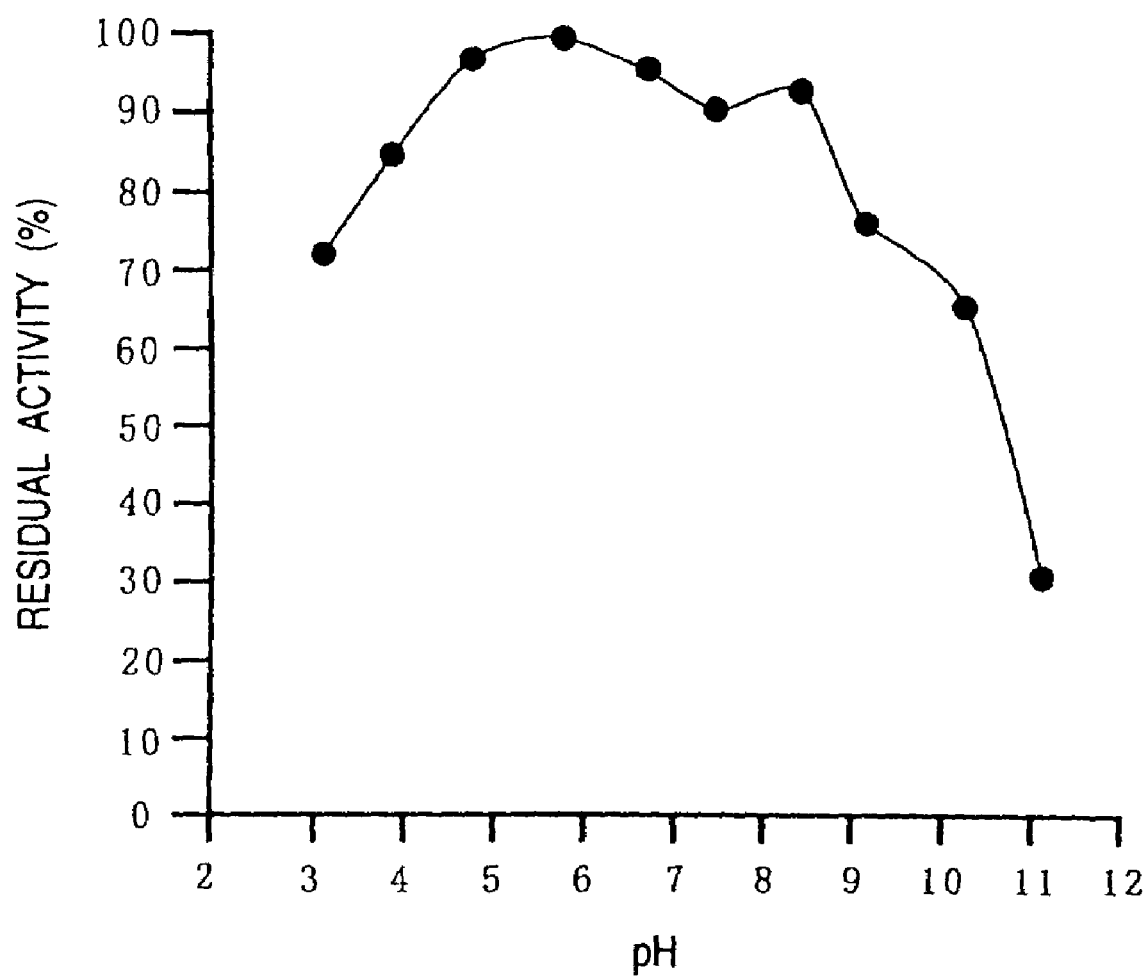
FIG. 4 is a graph showing pH stability of the protein-deamidating enzyme obtained from *Chryseobacteriuum gleum* JCM 2410.

(4) Measurement of pH stability: A 22 μl portion of enzyme solution containing 0.75 μg of the protein-deamidating enzyme (in 40 mM Britton-Robinson buffer solution having a pH value of from 3 to 12) was treated at 30° C. for 18 hours. Thereafter, the remaining enzyme activity was measured. The results are shown in FIG. 4.

Figure 5:
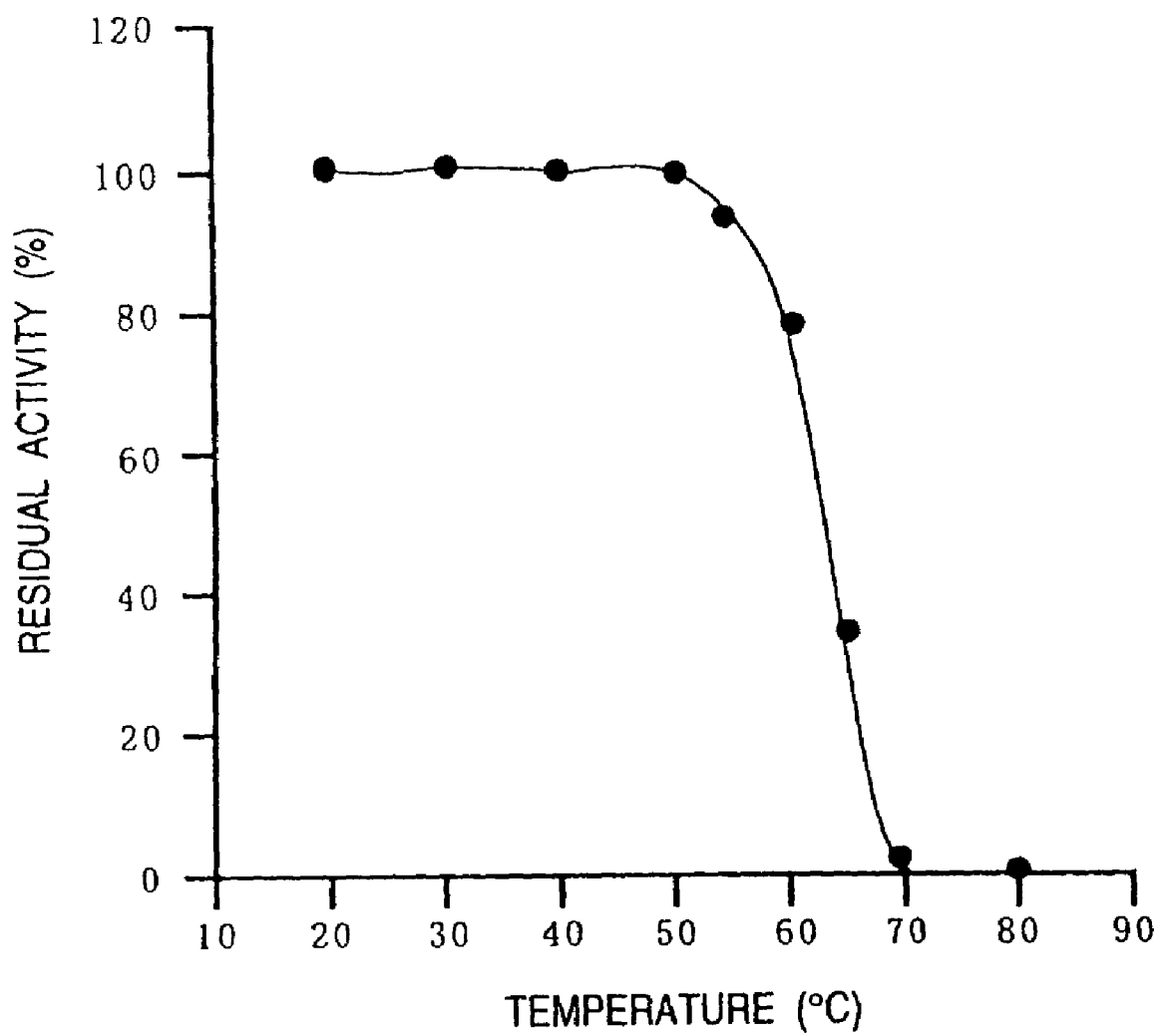
FIG. 5 is a graph showing temperature stability of the protein-deamidating enzyme obtained from *Chryseobacterium gleum* JCM 2410.

(5) Measurement of temperature stability: A 43 μl portion of enzyme solution containing 1.76 μg of the protein-deamidating enzyme [in 50 mM phosphate buffer solution (pH 7.0)] was allowed to stand at each temperature for 10 minutes, and then the remaining enzyme activity was measured. The results are shown in FIG. 5.

(6) Substrate specificity: A 100 μl portion of each of 1% solutions of various proteins used as the substrates was mixed with 10 μl of a protein-deamidating enzyme solution (10 mU), and 18 hours of the reaction was carried out at 37° C. As a control, the same treatment was carried out using water instead of the enzyme solution, and the amount of released ammonia was measured. The amount of released ammonia when water was added was subtracted from the amount of released ammonia when the enzyme solution was added, with the results shown in Table 2. When a portion of the reaction mixture after completion of the reaction was subjected to SDS-PAGE and compared with the control, increased or decreased molecular weight of the protein was not found. This result means that the enzyme of the present invention is a novel enzyme which can be distinguished from known transglutaminase and protease.

TABLE 2

| Protein | Released ammonia (mM) |
| --- | --- |
| Casein | 2.45 |
| Gluten | 1.85 |
| Soybean powder | 0.10 |
| Corn meal | 0.12 |
| β-Lactoglobulin | 0.65 |
| Ovalbumin | 0.24 |

(7) Measurement of isoelectric point: The isoelectric point was measured by the electrofocusing using Ampholine (600 V, 4° C., 48 hours). As a result, the enzyme of the present invention had an isoelectric point of 10.2.

Next, the method of the present invention for the modification of protein using the aforementioned protein-deamidating enzyme is described in detail.

The protein-deamidating enzyme of the present invention is allowed to act upon various proteins. Any type of protein can be used, with the proviso that it undergoes action of the aforementioned enzyme, and its examples are plant proteins obtained from beans and cereals and animal proteins which include milk proteins such as casein and β-lactoglobulin, egg proteins such as ovalbumin, meat proteins such as myosin and actin, blood proteins such as serum albumin and tendon proteins such as gelatin and collagen. Also included are partially hydrolyzed proteins obtained by chemical treatment with an acid or an alktli or by enzymatic treatment (e.g., with a protease), chemically modified proteins with various reagents and synthesized peptides.

These substrate proteins are subjected to the reaction in the form of solution, slurry or paste, but their concentrations are not particularly limited and optionally decided depending on the desired properties and conditions of the deamidated protein of interest. Also, the solution, slurry or paste of each substrate protein is not limited to an aqueous solution and may be in the form of emulsion with oil and fat and, as occasion demands, may contain additives such as salts, saccharides, proteins, perfumes, moisture keeping agents and coloring agents.

The reaction conditions such as amount of the enzyme, reaction time and temperature and pH of the reaction solution are not particularly limited too, but the reaction may be generally carried out using the enzyme in an amount of from 0.1 to 100 units, preferably from 1 to 10 units, based on 1 g of protein, at a reaction temperature of from 5 to 80° C., preferably from 20 to 60° C., at a reaction solution pH of from 2 to 10, preferably from 4 to 8, and for a period of from 10 seconds to 48 hours, preferably from 10 minutes to 24 hours. In addition, these conditions can be optionally changed depending, for example, on the purity of the enzyme to be used and the kind and purity of the substrate protein to be used. These reaction conditions are also applied to various uses of the enzyme of the present invention described in the following.

Thus, the action of the protein-deamidating enzyme of the present invention upon various proteins renders possible direct deamidation of amido groups in the protein. As the results, negative charge of the thus deamidated protein increases, which accompanies reduced pI, increased hydration ability and increased electrostatic repulsion. Also, changes in the higher-order structure of protein result in the increase of surface hydrophobic property. These effects result in the improvement of functionality of protein, such as increment of solubility and dispersibility, increment of foamability and foam stability and increment of emulsification ability and emulsification stability.

Thus, the protein having improved functionality greatly expands its use mainly in the field of food. A number of plant proteins show poor functionality such as solubility, dispersibility and emulsification ability particularly under weakly acidic condition which is the pH range of general food, so that they cannot be used in many food articles which include acidic drinks such as coffee whitener and juice, and dressing, mayonnaise and cream. However, when a plant protein having poor solubility, such as wheat gluten, is deamidated by the present invention, its solubility and dispersibility are increased, so that its use in these unsuited food articles becomes possible and it can be used as tempura powder having high dispersibility.

The enzyme of the present invention can also be used for the improvement of dough in the field of bakery and confectionery. For example, a dough material having high gluten content has problems in terms of handling and mechanical characteristics of the dough because of its low extensibility, as well as volume and quality of the finished bread. These problems can be resolved by improving the extensibility through the deamidation of gluten with this enzyme. Also, the deamidated gluten shows the effect as an emulsifying agent, so that bread producing characteristics such as keeping quality and softness are also improved. In addition, a dough material containing deamidated gluten has low plasticity and excellent extensibility, so that this is suitable for the production of crackers, biscuits, cookies, pizza pies or crusts of pie, and the enzyme of the present invention can be used in their production. For this purpose, the enzyme of the present invention is used generally in an amount of from 0.01 unit/kg to 10,000 units/kg, preferably from 0.1 unit/kg to 150 units/kg, based on the total weight of dough comprising wheat gluten and water, and they are mixed in the usual way.

Still more, when a protein in food, which causes allergy, a non-resistant disease or a genetic disease, is treated with the enzyme of the present invention, its toxicity and allergenic property can be removed or reduced. In the case of food allergy, most of the allergen peptides generally have high hydrophobic property. When they are converted into hydrophilic peptides by their treatment with the enzyme of the present invention, the allergenic property is removed or reduced. Particularly, large effect can be obtained when an allergen peptide contains glutamine residue such as the case of a wheat gluten allergen.

Still more, when a protein is deamidated by the enzyme of the present invention, mineral-sensitivity of the protein is reduced, so that the soluble mineral content in a protein-mineral solution is increased and absorption of minerals in the human body can be improved. It is well known in general that absorption of calcium contained in food by the human body is improved when calcium is solubilized using an organic acid or casein phosphopeptide. Based on the same mechanism, it is possible to solubilize a large quantity of calcium by deamidation of the protein by the enzyme of the present invention. Using the deamidated protein, high mineral (e.g., calcium) containing drinks and a mineral (e.g., calcium) absorption enhancing agents can be produced.

Also, in the case of the production of amino acid based condiments (HAP (Hydrolized Animal Protein) and HVP (Hydrolyzed Vegetable Protein)), bean paste (miso) or soy sauce, other effects such as reduction of bitterness, improvement of protein hydrolyzing ratio by protease and increase of the glutamic acid content can be obtained. It is well known in general that the cause of bitterness is originated from hydrophobic peptides, so that the deamidation renders possible reduction of bitter peptides. It is known also that a peptide having glutamic acid on its N-terminal has the effect to mask bitterness. In addition, since primary structure and higher-order structure of a material protein are changed by deamidation, protease-sensitivity of the protein can also be increased. As the results, the low degradation ratio, as a problem involved in the enzymatic production of HAP and HVP, can also be improved. On the other hand, reduction of the glutamic acid content caused by the formation of pyroglutamic acid is another problem in the production of HAP and HVP. Pyroglutamic acid is formed by the intramolecular cyclization of free glutamine, but it can be prevented by deamidation of the material protein and, as the result, the glutamic acid content is increased.

Still more, the enzyme of the present invention can be used as an agent for use in the control of the transglutaminase reaction. Transglutaminase is broadly used as a protein modifying agent, namely as a cross-linking enzyme, in the field of food and other industrial fields. The purpose of the use of transglutaminase is to obtain gelled protein products by the protein cross-linking reaction of the enzyme or to improve functionality of protein, but it is difficult to obtain a product having desired cross-linking degree and functionality in response to respective use and object, namely to control the cross-linking reaction such as termination of the reaction at an appropriate stage. Particularly in the case of the modification of proteins for food use, it is not desirable to add generally known transglutaminase inhibitors such as EDTA, ammonium chloride and SH reagents.

It is possible to terminate the transglutaminase reaction by adding the protein-deamidating enzyme of the present invention at a desired stage during the reaction of transglutaminase. That is, the transglutaminase reaction can be stopped by converting glutamine residues which are the target of the transglutaminase reaction in the substrate protein into glutamic acid residues by the protein-deamidating enzyme.

In that case, it is necessary that the affinity of the protein-deamidating enzyme for glutamine residues in a protein as its substrate is higher than that of transglutaminase, but the latter case of reaction requires the $\epsilon$-amino group of lysine in addition to glutamine residues while the former case requires only water other than the glutamine residues, which is abundantly present in the reaction environment, so that it is believed that the reaction of protein-deamidating enzyme generally precedes the reaction of transglutaminase. As a matter of course, a modified or gelled protein having desired cross-linking degree can be obtained by appropriately treating a substrate protein with the protein-deamidating enzyme to effect conversion of desired glutamine groups into glutamic acid residues and then subjecting the thus treated protein to the transglutaminase reaction.

The protein-deamidating enzyme of the present invention can also be used as a reagent for use in the functional modification of protein, namely for use in protein engineering. When the substrate protein is an enzyme, enzymatic, chemical and physicochemical properties of the enzyme can be modified. For example, when an enzyme protein is deamidated by the enzyme of the present invention, isoelectric point of the enzyme protein is reduced so that its pH stability can be modified. Also, other properties-of the enzyme such as substrate affinity, substrate specificity, reaction-speed, pH-dependency, temperature-dependency and temperature stability can be modified by changing the structure or electric environment of its active site.

It also can be used as reagents for analyses and studies of protein, such as a reagent for use in the determination of amide content of protein and a reagent for use in the solubilization of protein.

In addition, the enzyme of the present invention can be used for the improvement of extraction and concentration efficiencies of cereal and bean proteins. In general, proteins of cereals and beans such as wheat and soybean are mostly insoluble in water and cannot therefore be extracted easily, but such proteins can be extracted easily and high content protein isolates can be obtained when these proteins are solubilized by treating a suspension of wheat flour or soybean flour with the enzyme of the present invention.

In the case of soybean protein, when the protein is generally extracted from defatted soybean powder or flakes (protein content, about 50%), the protein is firstly insolubilized by a heat treatment, an ethanol treatment or an isoelectric point treatment at around pH 4.5, and then soluble polysaccharides are removed to obtain a soybean protein concentrate having a protein content of about 70%. When protein of more higher purity is desired, it is prepared by suspending or dissolving soybean powder or the concentrate in a dilute alkali solution to dissolve the protein and then removing insoluble substances. This product is called soybean protein isolate and contains about 90% of the protein. These soybean protein products are applied to various food articles such as ham, sausages and baby food, utilizing emmulsifying activity, gelling propety, and water-retaining property as well as high nutrition of the soybean protein When the enzyme of the present invention is used in producing these soybean protein products, not only the yield is improved due to the increased solubility of protein but also high concentration protein products can be produced. Since the protein products obtained in this manner are deamidated, they have excellent functionality. In consequence, they can exert excellent effects when used in various food articles such as meat or fish products and noodles, and their use renders possible production of food articles having new texture and functionality.

The following describes the protein-deamidating enzyme of the present invention, a gene which encodes the protein-deamidating enzyme, a recombinant vector which contains said gene, a transformant transformed with said vector and a method for the production of the protein-deamidating enzyme, which comprises culturing said transformant in a medium, thereby allowing the transformant to produce the protein-deamidating enzyme, and subsequently collecting the protein-deamidating enzyme from the culture mixture.

Regarding the protein-deamidating enzyme of the present invention, all of the protein-deamidating enzymes which can be obtained by the aforementioned protein-deamidating enzyme production methods are included, in which particularly preferred one is a polypeptide which has the amino acid sequence of Sequence No. 6 shown in the Sequence Listing attached, wherein one or more amino acid residues of the amino acid sequence may be modified by at least one of deletion, addition, insertion and substitution, and more preferred one is a polypeptide which has the amino acid sequence of Sequence No. 6 shown in the Sequence Listing.

Examples of the gene which encodes the protein-deamidating enzyme of the present invention include a gene which can be obtained from a microorganism capable of producing said protein-deamidating enzyme by cloning of said gene and a gene which has a certain degree of homology with said gene. Regarding the homology, a gene having a homology of at least 60% or more, preferably a gene having a homology of 80% or more and more preferably a gene having a homology of 95% or more can be exemplified. The following nucleotide (DNA or RNA) is desirable as the gene which encodes the protein-deamidating enzyme of the present invention.

A nucleotide which comprises a nucleotide being selected from the following nucleotides (a) to (g) and encoding a polypeptide having the activity to deamidate amido groups in protein;

(a) a nucleotide which encode a polypeptide having the amino acid sequence of Sequence No. 6 shown in the Sequence Listing, (b) a nucleotide which encode a polypeptide having the amino acid sequence of Sequence No. 6 shown in the Sequence Listing, wherein one or more amino acid residues of the amino acid sequence are modified by at least one of deletion, addition, insertion and substitution, (c) a nucleotide which has the nucleotide sequence of Sequence No. 5 shown in the Sequence Listing, (d) a nucleotide which has the nucleotide sequence of Sequence No. 5 shown in the Sequence Listing, wherein one or more bases of the nucleotide sequence are modified by at least one of deletion, addition, insertion and substitution, (e) a gene which hybridizes with any one of the aforementioned nucleotides (a) to (d) under a stringent condition, (f) a nucleotide which has homology with any one of the aforementioned nucleotides (a) to (d), and (g) a nucleotide which is degenerate with respect to any one of the aforementioned nucleotides (a) to (f).

The gene which encodes the protein-deamidating enzyme of the present invention can be prepared from the aforementioned microorganism capable of producing the protein-deamidating enzyme by carrying out cloning of said gene in the following manner. Firstly, the protein-deamidating enzyme of the present invention is isolated and purified from a microorganism capable of producing the protein-deamidating enzyme by the aforementioned method and information on its partial amino acid sequence is obtained.

Regarding the determination method of a partial amino acid sequence, it is effective to carry out a method in which purified protein-deamidating enzyme is directly applied to an amino acid sequence analyzer (such as Protein Sequenser 476A, manufactured by Applied Biosystems) by Edman degradation method [*J. Biol. Chem.*, vol. 256, pp. 7990-7997 (1981)], or a method in which limited hydrolysis of the protein-deamidating enzyme is carried out using a proteolytic enzyme, the thus obtained peptide fragments are isolated and purified and then amino acid sequences of the thus purified peptide fragments are analyzed.

Based on the information of the thus obtained partial amino acid sequences, the protein-deamidating enzyme gene is cloned. In general, the cloning is carried out making use of a PCR method or a hybridization method.

When a hybridization method is used, the method described in "Molecular Cloning, A Laboratory Manual" (edit. by T. Maniatis et al., Cold Spring Harbor Laboratory, 1989) may be used.

When a PCR method is used, the following method can be used.

Firstly, a gene fragment of interest is obtained by carrying out PCR reaction using genomic DNA of a microorganism capable of producing the protein-deamidating enzyme as the template and synthetic oligonucleotide primers designed based on the information of partial amino acid sequences. The PCR method is carried out in accordance with the method described in "PCR Technology" (edit. by Erlich H. A., Stockton Press, 1989). When nucleotide sequences of the thus amplified DNA fragments are determined by a generally used method such as the dideoxy chain termination method, a sequence which corresponds to the partial amino acid sequence of the protein-deamidating enzyme is found in the thus determined sequences, in addition to the sequences of synthetic oligonucleotide primers, so that a part of the protein-deamidating enzyme gene of interest can be obtained. As a matter of course, a gene which encodes complete protein-deamidating enzyme can be cloned by further carrying out a cloning method such as the hybridization method using the thus obtained gene fragment as a probe.

In Example 26 of this specification, a gene coding for the protein-deamidating enzyme was determined by the PCR method using *Chryseobacterium gleum* JCM 2410. Complete nucleotide sequence of the gene coding for the protein-deamidating enzyme originated from *Chryseobacterium gleum* JCM 2410 is shown in the Sequence No. 5, and the amino acid sequence encoded thereby was determined to be the sequence shown in the Sequence No. 6. In this connection, there are countless nucleotide sequences which correspond to the amino acid sequence shown in the sequence No. 6, in addition to the nucleotide sequence shown in the Sequence No. 5, and all of these sequences are included in the scope of the present invention.

The gene of interest can also be obtained by chemical synthesis based on the information of the amino acid sequence shown in the Sequence No. 6 and the nucleotide sequence shown in the Sequence No. 5 (cf. *Gene*, 60(1), 115-127, (1987)).

Regarding the protein-deamidating enzyme gene of the present invention, a nucleotide which encode a polypeptide having the amino acid sequence of Sequence No. 6 shown in the Sequence Listing, wherein one or more amino acid residues of the amino acid sequence are modified by at least one of deletion, addition, insertion and substitution, a gene which hybridizes with said nucleotide under a stringent condition, a nucleotide which has homology with said nucleotide and a nucleotide which is degenerate with respect to said nucleotide are also included in the present invention, with the proviso that the polypeptides encoded thereby have the protein-deamidating enzyme activity.

The term "under stringent condition" as used herein means the following condition. That is, a condition in which the reaction system is incubated at a temperature of from 50 to 65° C. for a period of from 4 hour to overnight in 6×SSC (1×SSC is a solution composed of 0.15 M NaCl and 0.015 M citric acid, pH 7.0) containing 0.5% SDS, 5×Denhart's (a solution composed of 0.1% bovine serum albumin (BSA), 0.1% polyvinyl pyrrolidone and 0.1% Ficoll 400) and 100 µg/ml of salmon sperm DNA.

By using the entire portion or a part of the protein-deamidating enzyme gene, whose complete nucleotide sequence has been revealed making use of *Chryseobacterium gleum* JCM 2410, as a probe for hybridization, DNA fragments having high homology with the protein-deamidating enzyme gene of Sequence No. 5 can be selected from genomic DNA libraries or cDNA libraries of microorganisms capable of producing other protein-deamidating enzymes.

The hybridization can be carried out under the aforementioned stringent condition. For example, a genomic DNA library or a cDNA library obtained from a microorganism capable of producing a protein-deamidating enzyme is fixed on a nylon membrane, and the thus prepared nylon membrane is subjected to blocking at 65° C. in a pre-hybridization solution containing 6×SSC, 0.5% SDS, 5×Denhart's and 100 µg/ml of salmon sperm DNA. Thereafter, each probe labeled with $^{32}$P is added to the nylon membrane which is then incubated overnight at 65° C. The thus treated nylon membrane is washed in 6×SSC at room temperature for 10 minutes, in 2×SSC containing 0.1% SDS at room temperature for 10 minutes and then in 0.2×SSC containing 0.1% SDS at 45° C. for 30 minutes, subsequently subjecting the thus washed membrane to an auto-radiography to detect a DNA fragment which hybridizes with the probe in a specific fashion. Also, genes which show various degree of homology can be obtained by changing certain conditions such as washing.

On the other hand, primers for use in the PCR reaction can be designed from the nucleotide sequence of the gene of the present invention. By carrying out the PCR reaction using these primers, gene fragments having high homology with the gene of the present invention can be detected and the complete gene can also be obtained.

In order to determine whether the thus obtained gene encodes a polypeptide having the protein-deamidating enzyme activity of interest, the thus determined nucleotide sequence is compared with the nucleotide sequence coding for the protein-deamidating enzyme of the present invention or with its amino acid sequence, and the identity is estimated based on the gene structure and homology. Alternatively, it is possible to determine whether the gene encodes a polypeptide which has the protein-deamidating enzyme activity of interest by producing a polypeptide of the gene and measuring its the protein-deamidating enzyme activity.

The following method is convenient for producing a polypeptide having the protein-deamidating enzyme activity using the protein-deamidating enzyme gene of the present invention.

Firstly, transformation of a host is carried out using a vector containing the protein-deamidating enzyme gene of interest and then culturing of the thus obtained transformant is carried out under generally used conditions, thereby allowing the strain to produce a polypeptide having the protein-deamidating enzyme activity.

Examples of the host to be used include microorganisms, animal cells and plant cells. Examples of the microorganisms include *Escherichia coli*, microorganisms belonging to the genus *Bacillus, Streptomyces, Lactococcus*, etc., yeasts belonging to the genus *Saccharomyces, Pichia, Kluyveromyces*, etc., and filamentous fungi belonging to the genus, *Aspergillus, Penicillium, Trichoderma*, etc. Examples of animal cells include animal cells utilizing the baculovirus expression system.

Confirmation of the expression and expressed product can be made easily by the use of an antibody specific for the protein-deamidating enzyme, and the expression can also be confirmed by measuring the protein-deamidating enzyme activity.

As described in the foregoing, purification of the protein-deamidating enzyme from the transformant culture medium can be carried out by optional combination of centrifugation, UF concentration, salting out and various types of chromatography such as of ion exchange resins.

In addition, since the primary structure and gene structure of the protein-deamidating enzyme have been revealed by the present invention, it is possible to obtain a gene coding for the amino acid sequence of a natural protein-deamidating enzyme, in which one or more amino acid residues of the amino acid sequence are modified by at least one of deletion, addition, insertion and substitution, by introducing random mutation or site-specific mutation using the gene of the present invention. This method renders possible preparation of a gene coding for a protein-deamidating enzyme which has the protein-deamidating enzyme activity but its properties such as optimum temperature, temperature stability, optimum pH and pH stability, substrate specificity, etc. are slightly changed, and it also renders possible production of such protein-deamidating enzymes by means of gene engineering techniques.

Examples of the method for introducing random mutation include a chemical DNA treating method in which a transition mutation is induced to convert cytosine base into uracil base by the action of sodium hydrogensulfite [*Proceedings of the National Academy of Sciences of the USA*, vol. 79, pp. 1408-1412 (1982)], a biochemical method in which base substitution is induced during the step of double strand formation in the presence of [α-S] dNTP [*Gene*, vol. 64, pp. 313-319 (1988)] and a PCR method in which PCR is carried out by adding manganese to the reaction system to decrease accuracy of the nucleotide incorporation [*Analytical Biochemistry*, vol. 224, pp. 347-353 (1995)].

Examples of the method for introducing site-specific mutation include a method in which amber mutation is employed [gapped duplex method; *Nucleic Acids Research*, vol. 12, no. 24, pp. 9441-9456 (1984)], a method in which recognition sites of restriction enzymes are used [*Analytical Biochemistry*, vol. 200, pp. 81-88 (1992); *Gene*, vol. 102, pp. 67-70 (1991)], a method in which mutation of dut (dUTPase) and ung (uracil DNA glycosylase) is used [Kunkel method; *Proceedings of the National Academy of Sciences of the USA*, vol. 82, pp. 488-492 (1985)], a method in which amber mutation is induced using DNA polymerase and DNA ligase [oligonucleotide-directed dual amber (ODA) method: *Gene*, vol. 152, pp. 271-275 (1995); JP-A-7-289262 (the term "JP-A" used herein means an unexamined published Japanese patent application)], a method in which a host introduced with a DNA repair system is used (JP-A-8-70874), a method in which a protein capable of catalyzing DNA chain exchange reaction is used (JP-A-8-140685), a method in which PCR is carried out using two different primers for mutation use to which recognition sites of restriction enzymes are added (U.S. Pat. No. 5,512,463), a method in which PCR is carried out using a double-stranded DNA vector having an inactivated drug resistance gene and two different primers [*Gene*, vol. 103, pp. 73-77 (1991)] and a method in which PCR is carried out making use of amber mutation (WO 98/02535).

Also, site-specific mutation can be introduced easily by the use of commercially available kits. Examples of such kits include Mutan™-G (manufactured by Takara Shuzo) in which the gapped duplex method is used, Mutan™-K (manufactured by Takara Shuzo) in which the Kunkel method is used, Mutan™-Express Km (manufactured by Takara Shuzo) in which the ODA method is used and QuickChange™ Site-Directed Mutagenesis Kit (manufactured by STRATAGENE) in which primers for mutation use and *Pyrococcus furiosus* DNA polymerase are used, as well as TaKaRa LA PCR in vitro Mutagenesis Kit (manufactured by Takara Shuzo) and Mutan™ Super Express Km (manufactured by Takara Shuzo) as kits in which PCR is used.

Thus, the primary structure and gene structure of the protein-deamidating enzyme provided by the present invention render possible production of an inexpensive and high purity polypeptide having the protein-deamidating enzyme activity by means of gene engineering techniques.

In this connection, various literature and references are cited in the specification, and all of them are incorporated herein by references.

Examples of the present invention are given below by way of illustration and not by way of limitation. Unless otherwise noted, the term "%" used in the following means "W/V %".

EXAMPLE 1

*Chryseobacterium gleum* JCM 2410 was cultured on a shaker at 30° C. for 6 days using the aforementioned lactose medium. Time course of the culturing is shown in FIG. 1.

EXAMPLE 2

Figure 6:
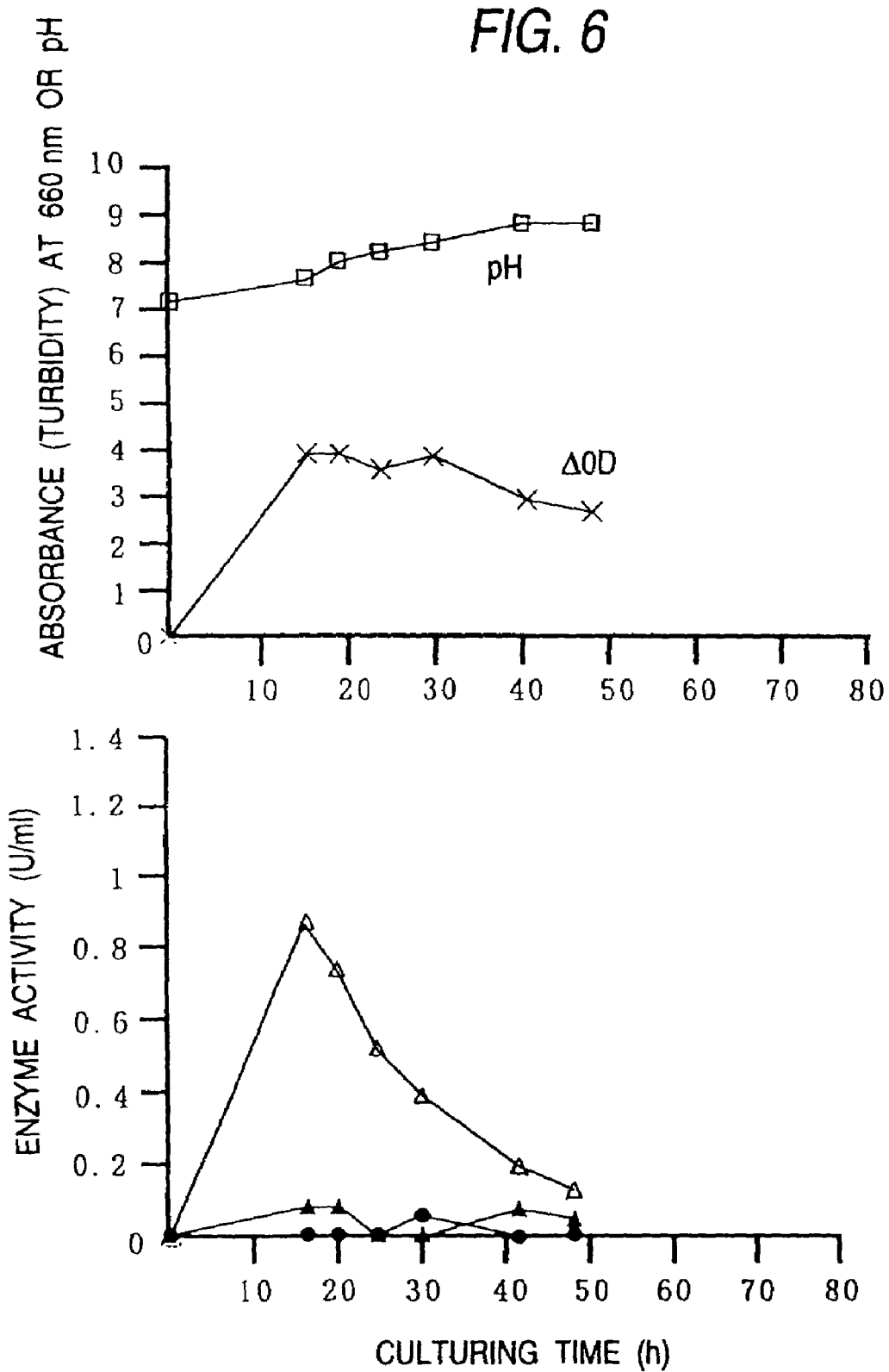
FIG. 6 is a graph showing time course of the culturing of *Chryseobacterium indologenes* IFO 14944 in lactose medium, in which the open square indicates changes in pH, the cross indicates changes in the absorbance of culture medium at 660 nm, the open triangle indicates changes in the protease activity when casein is used as the substrate, the closed circle indicates changes in the protein-deamidating enzyme activity when Z-Gln-Gly is used as the substrate and closed triangle indicates changes in the protein-deamidating enzyme activity when casein is used as the substrate.
Figure 7:
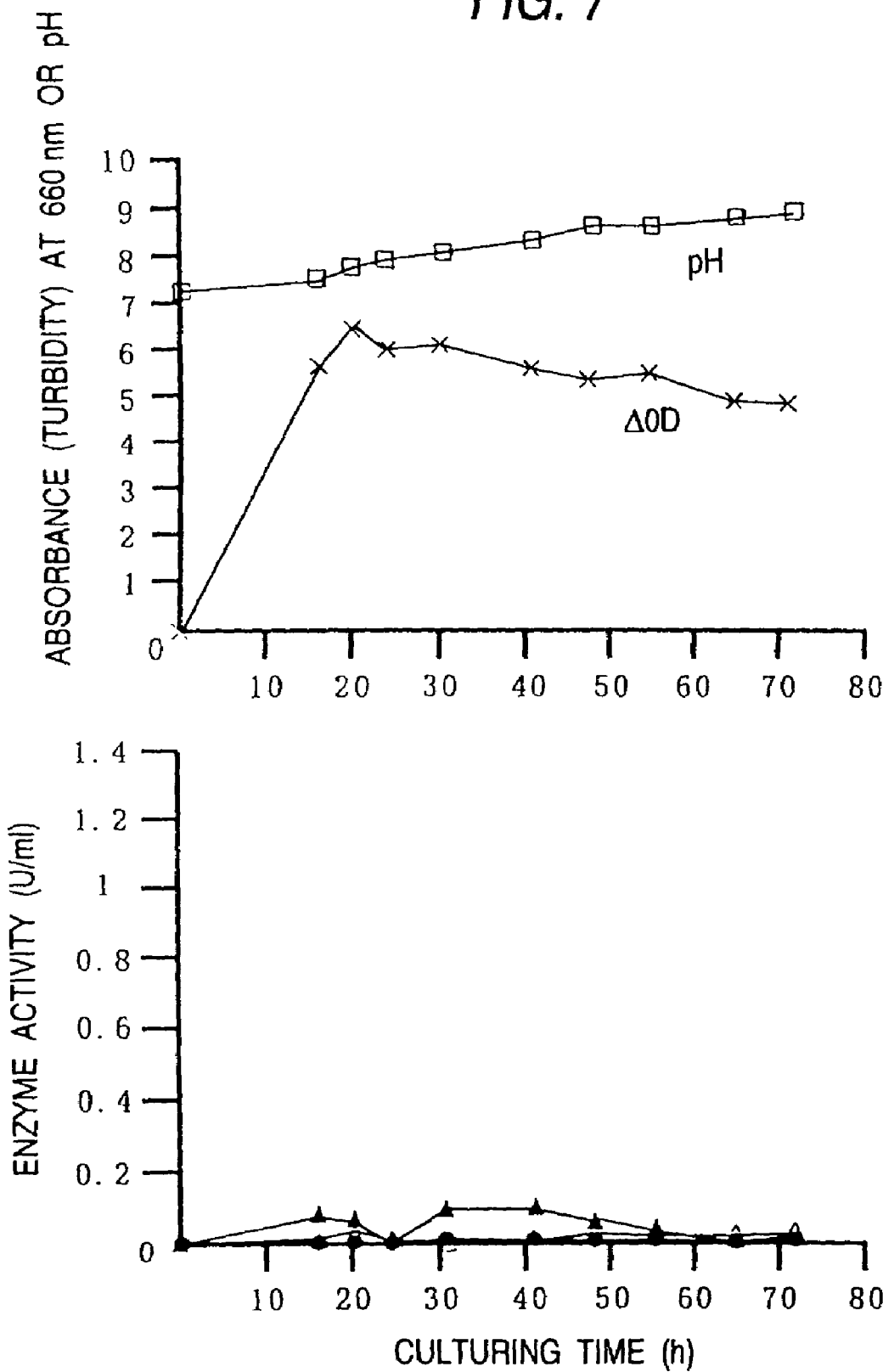
FIG. 7 is a graph showing time course of the culturing of *Chryseobacterium meningosepticum* IFO 12535 in lactose medium, in which the open square indicates changes in pH, the cross indicates changes in the absorbance of culture medium at 660 nm, the open triangle indicates changes in the protease activity when casein is used as the substrate, the closed circle indicates changes in the protein-deamidating enzyme activity when Z-Gln-Gly is used as the substrate and closed triangle indicates changes in the protein-deamidating enzyme activity when casein is used as the substrate.
Figure 8:
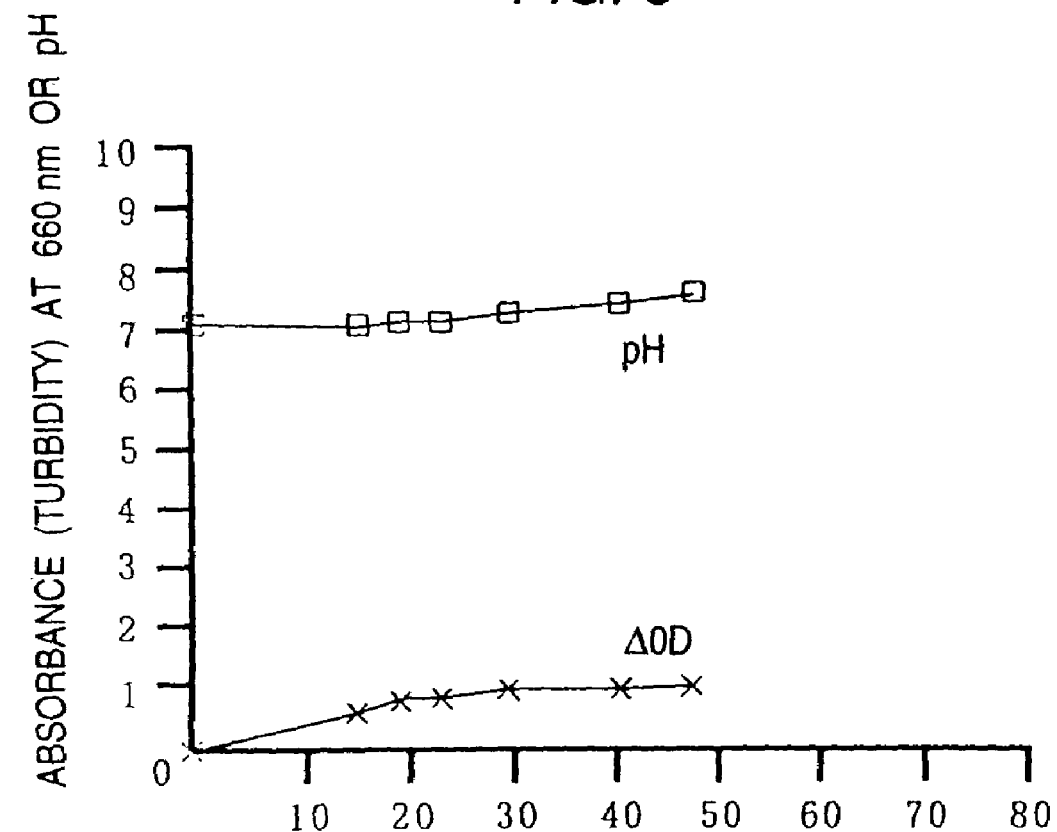
FIG. 8 is a graph showing time course of the culturing of *Chryseobacterium balustinum* IFO 15053 in lactose medium, in which the open square indicates changes in pH, the cross indicates changes in the absorbance of culture medium at 660 nm, the open triangle indicates changes in the protease activity when casein is used as the substrate, the closed circle indicates changes in the protein-deamidating enzyme activity when Z-Gln-Gly is used as the substrate and closed triangle indicates changes in the protein-deamidating enzyme activity when casein is used as the substrate.
Figure 8:
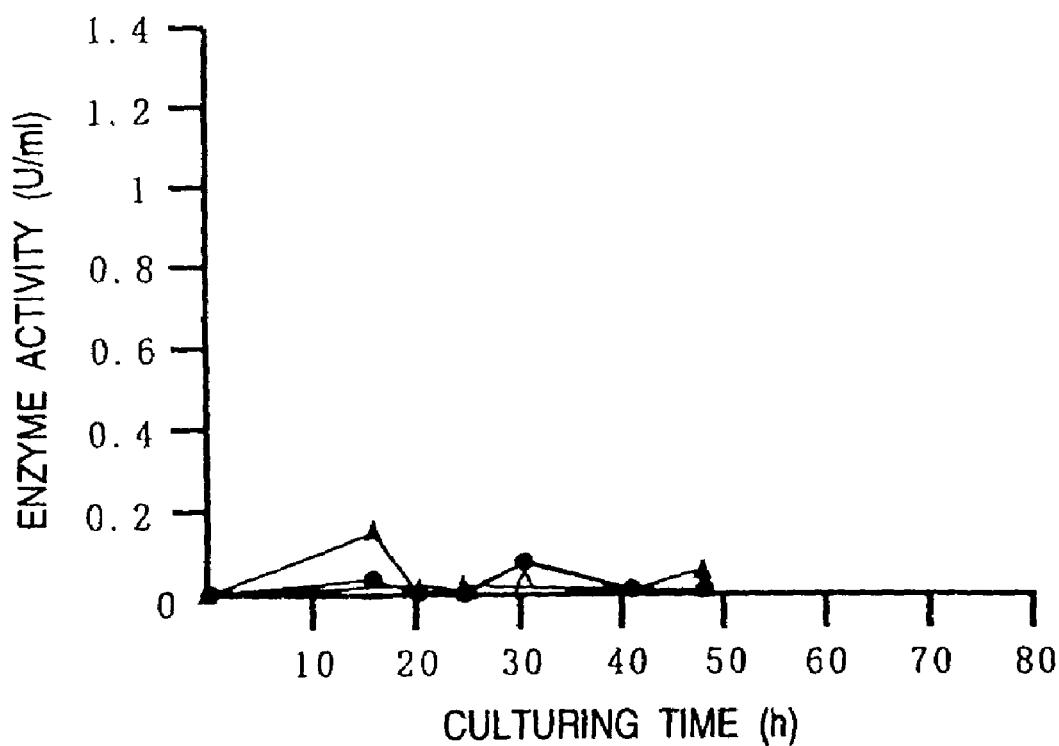

*Chryseobacterium indologenes* IFO 14944, *Chryseobacterium meningosepticum* IFO 12535 and *Chryseobacterium balustinum* IFO 15053 were cultured in the same manner as described in Example 1. Time courses of their culturing are shown in FIGS. 6 to 8.

EXAMPLE 3

*Flavobacterium aquatile* IFO 15052 was cultured in the same manner as described in Example 1. The protein-deamidating enzyme activity in the culture broth is shown in Table 3.

EXAMPLE 4

*Empedobacter brevis* IFO 14943 was cultured in the same manner as described in Example 1. The protein-deamidating enzyme activity in the culture broth is shown in Table 3.

EXAMPLE 5

Sphingobacterium spiritivorum IFO 14948 and Sphingobacterium heparinum IFO 12017 were cultured in the same manner as described in Example 1. The protein-deamidating enzyme activity in the culture broth is shown in Table 3.

EXAMPLE 6

Aureobacterium esteroaromaticum IFO 3751 was cultured in the same manner as described in Example 1. The protein-deamidating enzyme activity in the culture broth is shown in Table 3.

EXAMPLE 7

Myroides odoratus IFO 14945 was cultured in the same manner as described in Example 1. The protein-deamidating enzyme activity in the culture broth is shown in Table 3.

TABLE 3

| Strain | Culture time (h) | Deamidation activity (U/ml) | |
|---|---|---|---|
| | | Z-Gln-Gly | Casein |
| Flavobacterium aquatile IFO 15052 | 48 | 0.019 | 0.038 |
| Empedobacter brevis IFO 14943 | 20 | 0.040 | 0.149 |
| Sphingobacterium spiritivorum IFO 14948 | 20 | 0.057 | 0.078 |
| Sphingobacterium heparinum IFO 12017 | 48 | 0.047 | 0.031 |
| Aureobacterium esteroaromaticum IFO 3751 | 31 | 0.003 | 0.019 |
| Myroides odoratus IFO 14945 | 41 | 0.005 | 0.026 |

Production of the protein-deamidating enzyme was confirmed in each of the strains used in Examples 1 to 7.

EXAMPLE 8

When the strains used in Examples 1 to 5 were cultured in the same manner using the following medium instead of the lactose medium, production of the protein-deamidating enzyme was found in each strain.

| | |
|---|---|
| Yeast extract | 0.25% |
| Polypeptone | 0.3% |
| Casein sodium | 0.25% |
| $Na_2HPO_4 \cdot 12H_2O$ | 0.3% |
| $MgSO_4 \cdot 7H_2O$ | 0.02% |
| (pH 7.0) | |

EXAMPLE 9

The culture broth obtained after 24 hours of culturing in Example 1 was subjected to 15 minutes of centrifugation at 4° C. and at 12,000 rpm (22,200×g) to remove cells, and the thus obtained centrifugation supernatant was concentrated to about 17 times using an ultrafiltration membrane (SEP-0013, manufactured by Asahi Chemical Industry) and then dialyzed overnight at 4° C. against 10 mM sodium phosphate buffer solution (pH 6.5) containing 2.0 M NaCl. The thus formed precipitate was removed by 15 minutes of centrifugation at 4° C. and at 10,000 rpm (12,300 ×g), and the thus obtained centrifugation supernatant was applied to a Phenyl-Sepharose CL-6B column (manufactured by Pharmacia) which had been equilibrated with 10 mM sodium phosphate buffer solution (pH 6.5) containing 2.0 M NaCl, and the adsorbed protein was eluted by a linear NaCl density gradient of from 2.0 M to 0 M.

Fractions having protein deamidation activity were combined, concentrated using the ultrafiltration membrane and then applied to a Sephacryl S-100 column which had been equilibrated with 10 mM sodium phosphate buffer solution (pH 6.5) containing 0.6 M NaCl and 0.05% Tween 20, and the elution was carried out using the same buffer. Fractions having protein deamidation activity were combined, concentrated using the ultrafiltration membrane and then dialyzed against distilled water, thereby obtaining a protein-deamidating enzyme solution.

Figure 9:
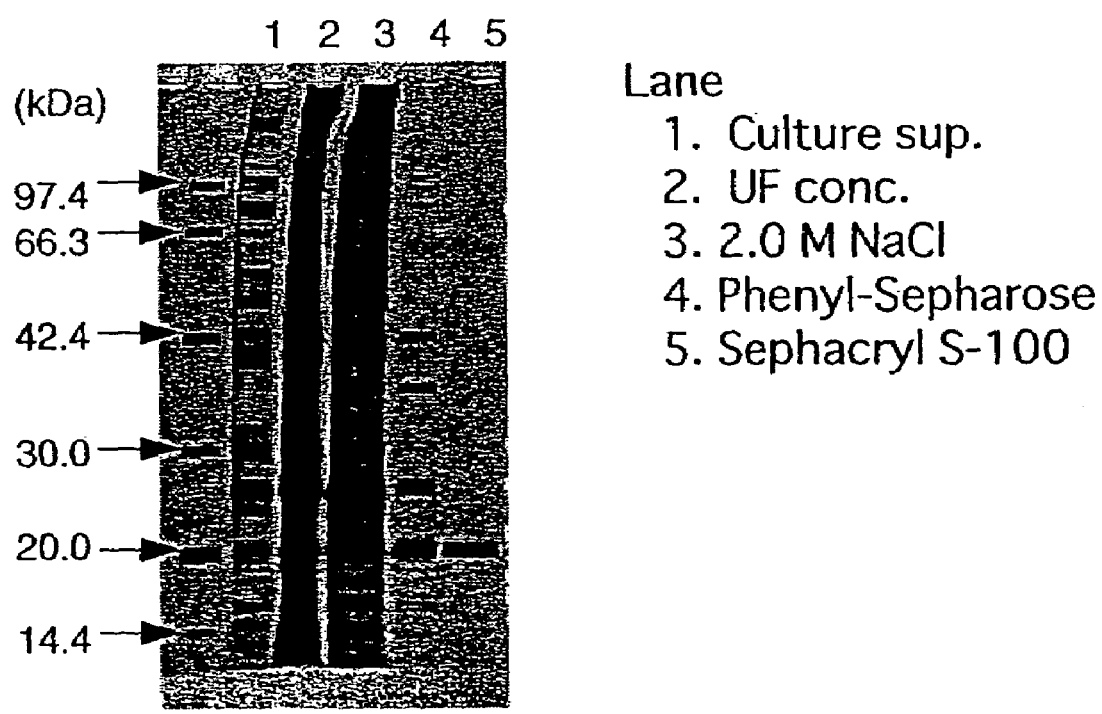
FIG. 9 is a photograph showing results of SDS-polyacrylamide gel electrophoresis in Example 9 using samples in respective steps of protein-deamidating enzyme purification.

Samples of purification steps were subjected to 10-20% SDS-polyacrylamide gel electrophoresis. The result is shown in FIG. 9. It is apparent that the purified enzyme sample (lane 5) is a single protein having a molecular weight of about 20 kDa by SDS-polyacrylamide gel electrophoresis.

When measured by the aforementioned assay methods (the method which uses Z-Gln-Gly as the substrate and the method which uses casein as the substrate), the thus obtained enzyme preparation showed the activities of 18.8 units/ml (Z-Gln-Gly as the substrate) and 14.0 units/ml (casein as the substrate). Transglutaminase activity and protease activity were not detected. In consequence, it is evident that the protease activity in the culture broth shown in FIG. 1 was completely removed by the aforementioned purification process. In addition, the enzyme preparation did not show glutaminase activity against free glutamine.

EXAMPLE 10

Each culture broth obtained in Examples 2 to 7 was purified in the same manner as described in Example 9. As a result, respective activities shown in Table 4 were obtained. Transglutaminase activity and protease activity were not detected in the thus obtained protein-deamidating enzymes. In consequence, it is evident that the protease activity in the culture broth was completely removed by the aforementioned purification process.

TABLE 4

| Strain | Deamidation activity (U/ml) | |
|---|---|---|
| | Z-Gln-Gly | Casein |
| Chryseobacterium indologenes IFO 14944 | 14.2 | 10.5 |
| Chryseobacterium meningosepticum IFO 12535 | 13.2 | 10.3 |
| Chryseobacterium balustinum IFO 15053 | 9.88 | 7.48 |
| Flavobacterium aquatile IFO 15052 | 3.97 | 3.09 |
| Empedobacter brevis IFO 14943 | 2.11 | 1.48 |
| Sphingobacterium spiritivorum IFO 14948 | 1.59 | 1.25 |
| Sphingobacterium heparinum IFO 12017 | 7.43 | 5.20 |
| Aureobacterium esteroaromaticum IFO 3751 | 1.44 | 1.15 |
| Myroides odoratus IFO 14945 | 3.06 | 2.36 |

EXAMPLE 11

Preparation of Deamidated Gluten

Figure 10:
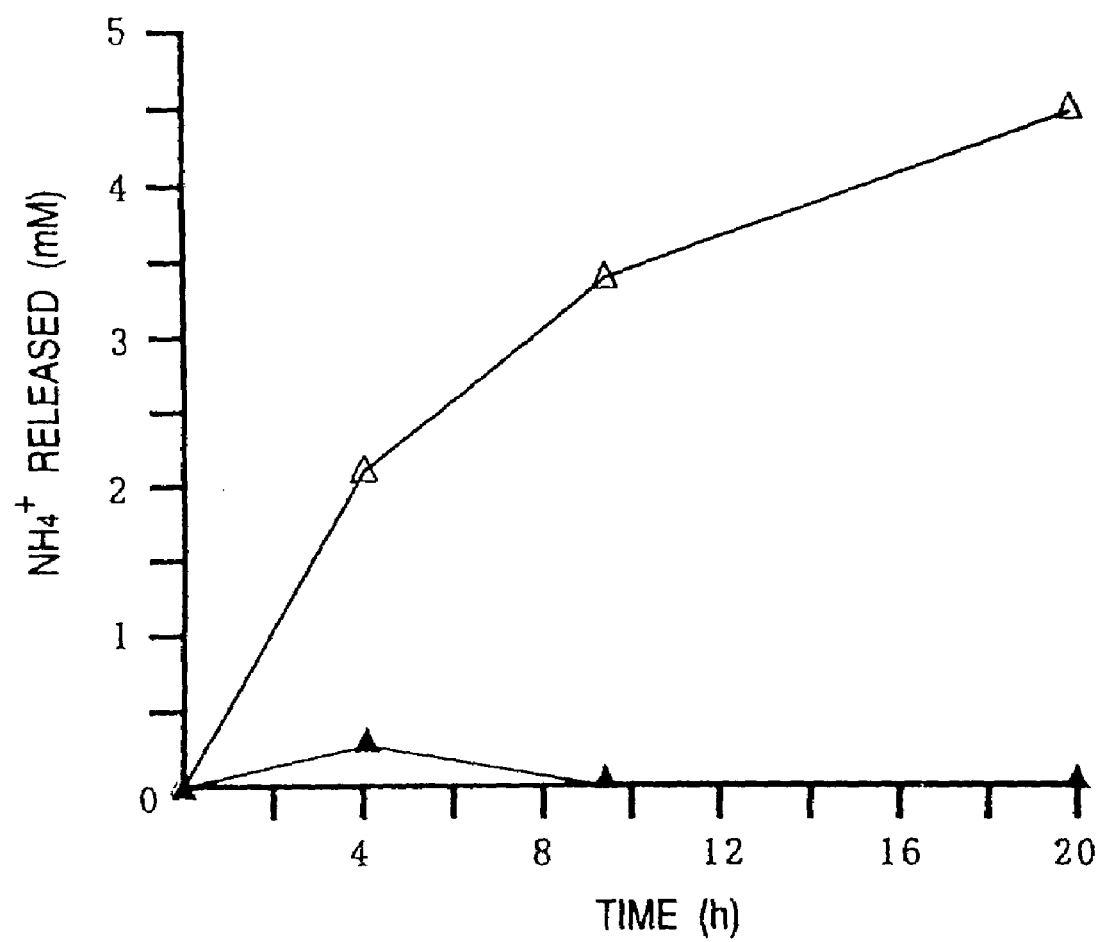
FIG. 10 is a graph showing releasing pattern of ammonia in Example 11, in which the open triangle indicates results when the protein-deamidating enzyme was added and the closed triangle indicates results of blank test.

A 1 g portion of wheat gluten was suspended in 100 ml of 176 mM sodium phosphate buffer (pH 6.5), 5 units of the protein-deamidating enzyme was added to the suspension and the mixture was allowed to undergo the enzyme reaction at 37° C. for 20 hours on a shaker. The releasing pattern of ammonia during this reaction is shown in FIG. 10. It can be understood from the drawing that the deamidation reaction was generated in the enzyme-added reaction system since ammonia was released with the passage of the reaction time, which is contrary to the reaction carried out in the absence of the enzyme as a control. After the reaction, this was dialyzed against distilled water and then freeze-dried to obtain deamidated gluten powder.

The resulting deamidated gluten had a deamidation percentage of 37.4%. The deamidation percentage was determined by measuring the amount of ammonia released in the solution after the reaction and showed as a percentage to the total amido content of wheat gluten. The total amido content of protein was determined by hydrolyzing the protein (1% w/v) in 2N hydrochloric acid at 100° C. for 2 hours and measuring ammonia release.

EXAMPLE 12

Improvement of Functionality (Solubility and Dispersibility) of Deamidated Gluten A 2.0 mg portion of each of the deamidated gluten powder obtained in Example 11 and enzyme-untreated gluten powder obtained by the control test was suspended and dissolved in 1.0 ml of 40 mM Britton-Robinson buffer having a pH value of from 3 to 12, shaken at room temperature for 30 minutes and then allowed to stand at room temperature for 30 minutes. After checking the pH value, this was centrifuged at a low speed of 3,000 rpm (760×g) for 10 minutes at 24° C., and the protein content in the thus obtained supernatant was measured by the BCA method. The protein content in the supernatant was used as an index of the dispersibility (*Methods of Testing Protein Functionality*, p. 25, edited by G. M. Hall, Blackie Academic & Professional, London, 1996).

The supernatant was further centrifuged at a high speed of 14,000 rpm (16,000 ×g) for 30 minutes at 24° C., the thus obtained supernatant was filtered through a 0.45 μm membrane and then the protein content in the resulting filtrate was measured by the BCA method. The protein content in the filtrate was used as an index of the solubility (*Methods of Testing Protein Functionality*, pp. 47-55, edited by G. M. Hall, Blackie Academic & Professional, London, 1996).

Figure 11:
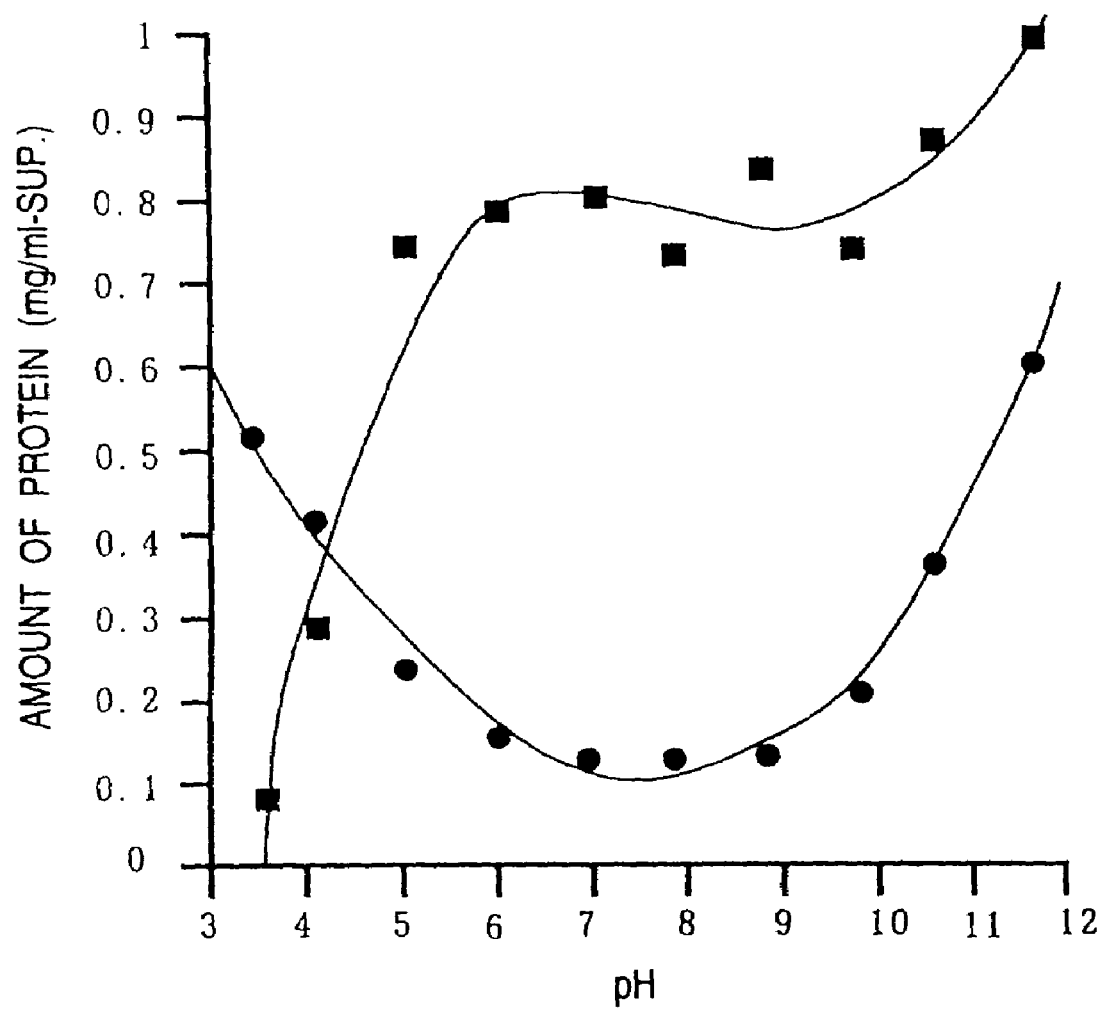
FIG. 11 is a graph showing dispersibility of deamidated gluten in Example 12, in which the closed square indicates results of gluten treated with the protein-deamidating enzyme and the closed circle indicates results of untreated gluten.
Figure 12:
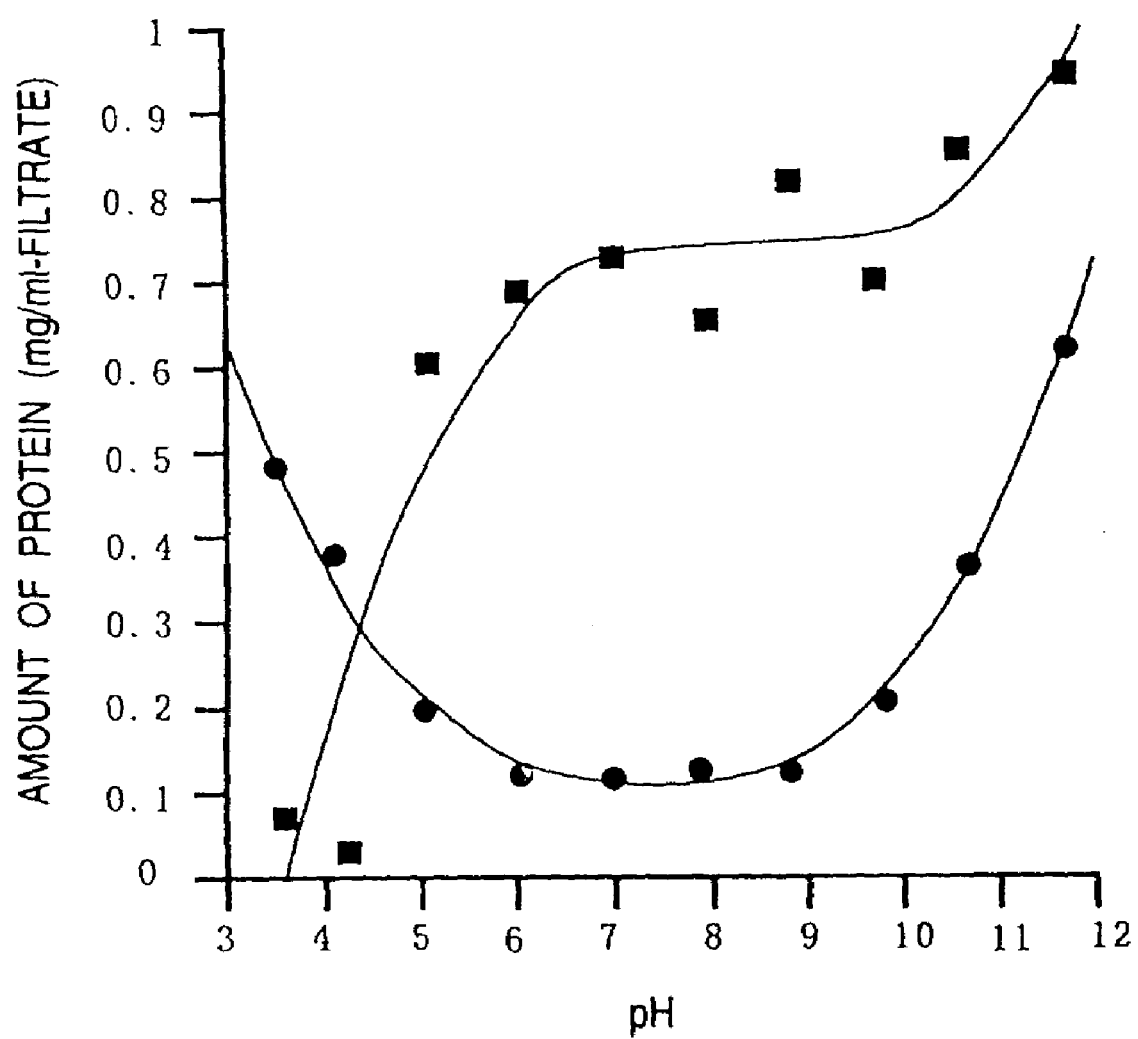
FIG. 12 is a graph showing solubility of deamidated gluten in Example 12, in which the closed square indicates results of gluten treated with the protein-deamidating enzyme and the closed circle indicates results of untreated gluten.

As is evident from the results shown in FIGS. 11 and 12, when compared with the enzyme-untreated gluten, the deamidated gluten has markedly improved dispersibility and solubility within a broad pH range of from around pH 4.2 to around pH 12.

EXAMPLE 13

Production of Coffee Whitener Using Deamidated Gluten

A 5 g portion of deamidated gluten produced in accordance with the method of Example 11 was mixed with 2 g of corn syrup, 0.4 g of polysorbate 60 and 51 g of water, and the mixture was heated at 40° C. and then mixed with 0.3 g of dipotassium hydrogenphosphate and heated to 80° C. A 6 g portion of partially hydrogenated coconut oil and 0.2 g of monoglyceride were added under melted state to the mixture solution, and the resulting mixture was hallowed to stand at 80° C. for 20 minutes, homogenized under a pressure of 211 kg/cm$^2$ and then cooled, thereby producing a coffee whitener containing deamidated gluten. This product showed a stable emulsion state, and showed excellent dispersibility, solubility and palatability when added to coffee.

EXAMPLE 14

Production of Tempura Flour

A 100 g portion of wheat flour was suspended in 1 liter of water, and the suspension was mixed with 10 units of the protein-deamidating enzyme, subjected to the enzyme reaction at 37° C. for 20 hours with shaking, dehydrated by centrifugation and then heat-dried to obtain deamidation-treated wheat flour. A 50 g portion of the thus obtained wheat flour was dissolved in 60 ml of water and used as a coating solution for tempura use. A prawn (*Penaeus orientalis*) (about 25 g) was floured, coated with the coating solution and then fried in a rapeseed/soybean mixture oil at 170 to 180° C. for 3 minutes. The prawn was also fried in the same manner using wheat flour which has not been treated with the protein-deamidating enzyme. The wheat flour treated with the protein-deamidating enzyme showed excellent dispersibility when the coating solution was prepared, and the thus obtained fry was markedly excellent in terms of eating touches such as hardness and crispness of the coating, as well as its appearance and taste.

EXAMPLE 15

Production of Premix

A premix for hot cake use having the following composition was prepared using the protein-deamidating enzyme-treated wheat flour which has been prepared in accordance with the method of Example 14.

| | |
|---|---|
| Protein-deamidating enzyme-treated wheat flour | 72.0% |
| Sugar | 20.0% |
| Expanding agent (sodium bicarbonate) | 1.5% |
| Oil and fat | 3.0% |
| Table salt | 1.0% |
| Gluconodeltalactone | 2.0% |
| Spice | 0.5% |

A 200 g portion of the thus prepared premix was put into a bowl to which were further added 150 ml of milk and 50 g of whole egg, and the contents were mixed by whipping to obtain a dough for hot cake use. A control dough was prepared in the same manner using untreated wheat flour. A 100 g portion of the thus obtained dough was spread in a circular form on a hot plate of 160° C., and its front side was baked for 4 minutes, and the back side for 2 minutes, thereby obtaining a hot cake.

Handling of the dough and softness, melting touch in the mouth and wetness of the hot cake were judged by a panel. As the results, all of these factors were superior to those of the control when the protein-deamidating enzyme-treated wheat flour was used.

EXAMPLE 16

Preparation of Bread Dough

A one loaf bread was produced by a no time method using the following formulation.

[Formulation]

| | | |
|---|---|---|
| Wheat flour | 100% | 2,000 g |
| Sugar | 15% | 100 g |
| Table salt | 2% | 40 g |
| Shortening | 4% | 80 g |
| Yeast | 3% | 60 g |
| Ascorbic acid | 20 ppm | 40 mg |
| Water | 69% | 1,380 ml |

Using the above formulation as the base, a protein-deamidating enzyme-added (7.5 units/1 kg wheat flour) group and an enzyme-free (control) group were prepared and compared.

[Steps]
(1) Mixing: 4 minutes at low speed→
  4 minutes at high speed→
  addition of shortening→
  1 minute at low speed→
  4 minute at medium speed→
  4 minutes at high speed
(2) Kneading Temperature: 27-29° C.
(3) Floor Time: 27° C., 30 minutes
(4) Separation: dough weight, 450 g
(5) Bench Time: 30 minutes
(6) Drying: 38° C., 3.5 cm on a bread case mold
(7) Baking: 230° C., 25 minutes In the protein-deamidating enzyme-added group, handling of the dough was excellent, and extensibility of the dough and softness of the baked bread were improved.

EXAMPLE 17

Preparation of Biscuit Dough

A biscuit dough of the following composition was prepared using protein-deamidating enzyme-treated wheat flour which has been prepared in accordance with the method of Example 14.

| | |
|---|---|
| Protein-deamidating enzyme-treated wheat flour | 100 g |
| Shortening | 16 g |
| Sugar | 50 g |
| Sodium bicarbonate | 0.81 g |
| Potassium bitartarate | 0.5 g |
| Water | 16 g |
| Egg | 2 g |

Mixing, molding and baking (180-220° C.) were carried out in the usual way to prepare hard biscuits. Handling of the dough and improvement of extensibility were significant, and eating touch of the prepared biscuits was also excellent.

EXAMPLE 18

Preparation of Deamidated casein

Figure 13:
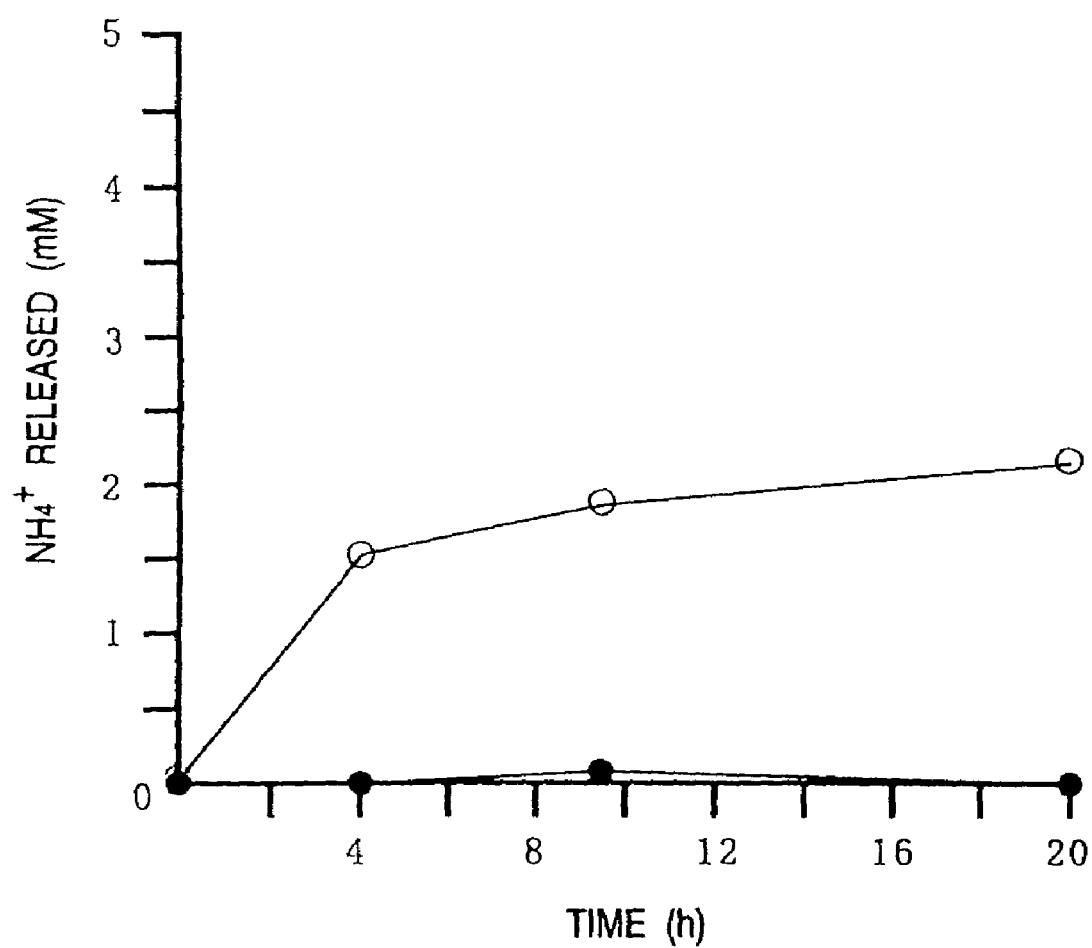
FIG. 13 is a graph showing releasing pattern of ammonia in Example 18, in which the open circle indicates results when the protein-deamidating enzyme was added and the closed circle indicates results of blank test.

A 1 g portion of milk casein was suspended in 100 ml of 176 mM sodium phosphate buffer (pH 6.5), 5 units of the protein-deamidating enzyme was added to the suspension and the mixture was allowed to undergo the enzyme reaction at 37° C. for 20 hours on a shaker. The releasing pattern of ammonia during this reaction is shown in FIG. 13. It can be understood from the drawing that the deamidation reaction was generated in the enzyme-added reaction system since ammonia was released with the passage of the reaction time, which is contrary to the reaction carried out in the absence of the enzyme as a control. After the reaction, this was dialyzed against distilled water and then freeze-dried to obtain deamidated casein powder.

The resulting deamidated casein had a deamidation percentage of 40.9%. The deamidation percentage was determined by measuring the amount of ammonia released in the solution after the reaction and showed as a percentage to the total amido content of casein. The total amido content of protein was determined by hydrolyzing the protein (1% w/v) in 2N hydrochloric acid at 100° C. for 2 hours and measuring ammonia release.

Figure 14:
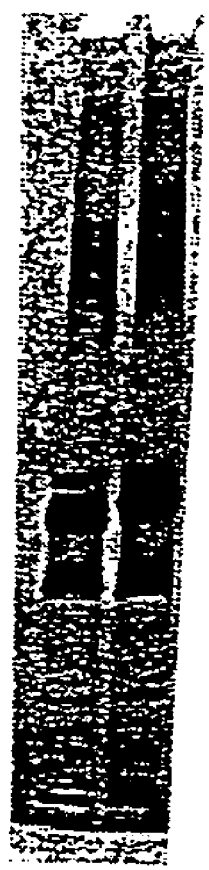
FIG. 14 is a photograph showing results of SDS-polyacrylamide gel electrophoresis of deamidated casein in Example 18.

The deamidated casein as well as an enzyme-untreated casein were subjected to 10-20% SDS-PAGE. The resulting pattern is shown in FIG. 14. It is clear that the molecular weight of the deamidated casein (lane 2) did not change, i.e., degradation or cross-linking was not occurred. Although a slight shift of deamidated casein band to higher molecular weight side is observed, it is considered that this shift was due to the increase in minus charges in protein by deamidation. In the presence of SDS, total minus charges of deamidated casein should be low compared to those of non-deamidated casein because the amount of SDS, which also has minus charges, binding to deamidated casein should be less than that to non-deamidated casein by electrostatic repulsion. The lower total minus charges of deamidated casein should cause reduced migration in the electophoresis.

EXAMPLE 19

Improvement of Calcium-Dependent Solubility of Deamidated Casein

A 2.0 mg portion of each of the deamidated casein powder obtained in Example 18 and enzyme-untreated casein powder obtained by the control test was suspended and dissolved in 10 mM Tris-HCl buffer (pH 7.1) containing calcium chloride in an amount of from 0 to 30 mM, shaken at room temperature for 30 minutes and then allowed to stand at room temperature for 30 minutes. This solution was centrifuged at a low speed of 3,000 rpm (760×g) for 10 minutes at 24° C., the resulting supernatant was further centrifuged at a high speed of 14,000 rpm (16,000×g) for 30 minutes at 24° C., the thus obtained supernatant was filtered through a 0.45 μm membrane and then the protein content in the resulting filtrate was measured by the BCA method. The protein content in the filtrate was used as an index of the calcium-dependent solubility.

Figure 15:
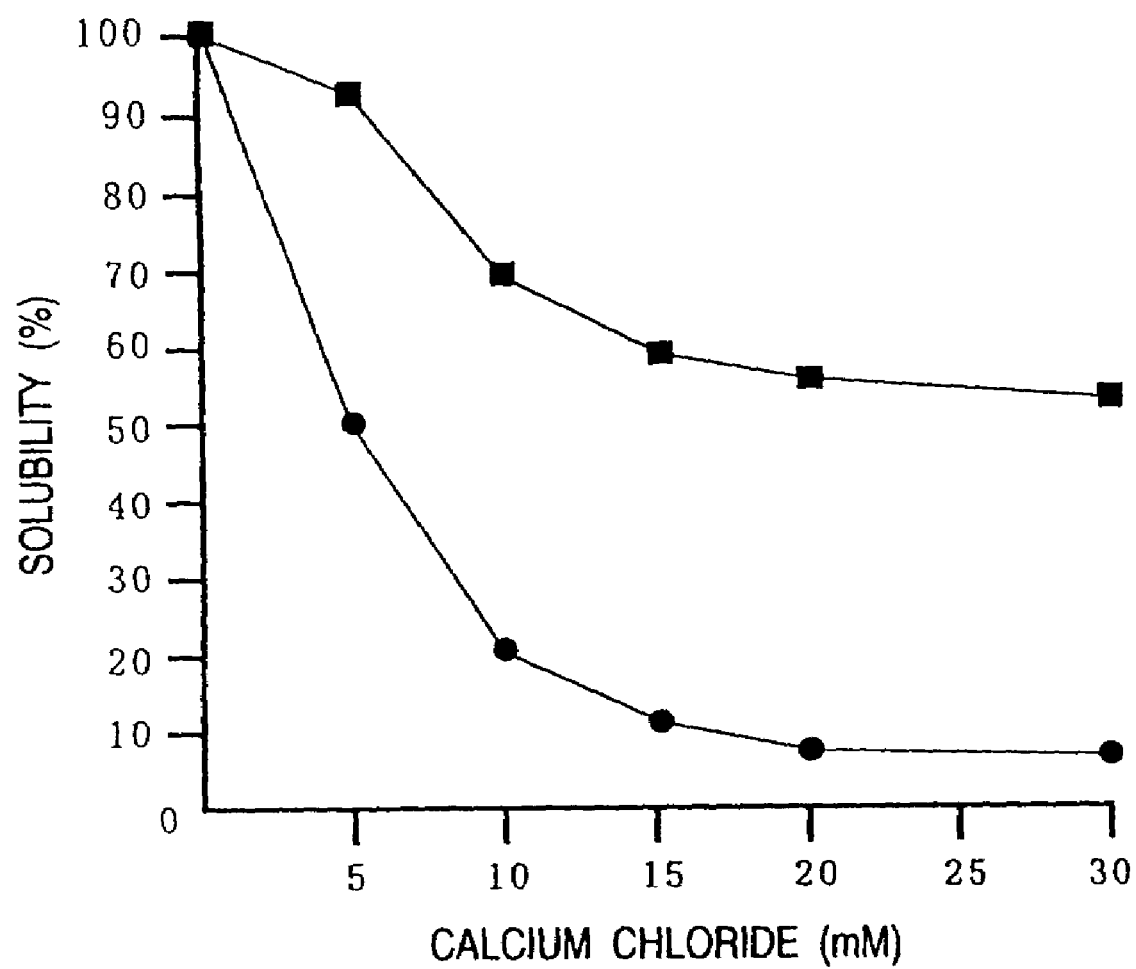
FIG. 15 is a graph showing calcium-dependent solubility of deamidated casein in Example 19, in which the closed square indicates results of casein treated with the protein-deamidating enzyme and the closed circle indicates results of untreated casein.

As is evident from the results shown in FIG. 15, when compared with the enzyme-untreated casein, the deamidated casein shows high solubility even in the presence of high concentration of calcium, so that its calcium-dependent solubility is markedly improved.

EXAMPLE 20

Production of Enzyme-Digested Liquid Seasoning

A 150 ml portion of 15% brine was added to 45 g of gluten to which were further added 50 units of the protein-deamidating enzyme, 0.1% of Glutaminase F100 (manufactured by Amano Pharmaceutical Co., Ltd.) and 0.75% of Protease M (manufactured by Amano Pharmaceutical Co., Ltd.), and the resulting mixture was allowed to undergo 3 to 4 days of the reaction at 45° C. After the reaction, the reaction mixture was heated at 90° C. for 20 minutes to prepare an enzyme-digested liquid seasoning. It was able to produce an excellent liquid seasoning in which the formation of bitter components was reduced due to the improvement of both decomposition ratio and decomposition rate, in comparison with a control liquid seasoning prepared in the same manner without adding the protein-deamidating enzyme.

EXAMPLE 21

Method for the Concentration and Recovery of Soybean Protein and Production of Deamidated Soybean Protein A 100 g portion of soybean flour was suspended and dissolved in 1 liter of water which was subsequently adjusted to pH 6.5 while stirring, mixed with 500 units of the protein-deamidating enzyme and then stirred at room temperature for 2 hours. After the reaction, this was adjusted to pH 8, stirred for 1 hour and then centrifuged at 10,000 rpm (12,300×g) for 30 minutes at room temperature to remove insoluble matter. In order to recover protein from the thus obtained supernatant, the supernatant was subjected to 30 minutes of heat treatment at 80° C. and then to 30 minutes of centrifugation at 10,000 rpm (12,300×g), and then the thus formed precipitate was recovered and dried to obtain protein powder. The protein content of this protein powder was 95%, and it was obtained with a high yield of about 40% from soybean flour.

EXAMPLE 22

Production of Sausage Using Deamidated Soybean Protein

The deamidated soybean protein produced in accordance with the method of Example 21 was subjected to a coagulation treatment by repeating its stirring, extrusion and rolling steps. The thus coagulated soybean protein was kneaded with meat materials and various spices according to the following formulation and then packed in casings in the usual way to produce sausages. The thus obtained product was markedly excellent in terms of palatability.

| | |
|---|---|
| Pork shoulder | 500 g |
| Beef round | 500 g |
| Pork ground fat | 100 g |
| Coagulated soybean protein | 100 g |
| Table salt | 25 g |
| Potassium nitrate | 3 g |
| Sugar | 5 g |
| Ajinomoto (sodium glutamate) | 3 g |
| White pepper | 3 g |
| Nutmeg | 4 g |
| Cinnamon | 0.5 g |
| Onion juice | 5 g |

EXAMPLE 23

Use as a Transglutaminase Reaction Controlling Agent

A 12.5 μl portion of a solution containing 0.0125 unit of *Streptoverticillium transglutaminase* (prepared in accordance with the method described in *Agric. Biol. Chem.*, vol. 53, no. 10, pp. 2613-2617, 1989) was added to 25 μl of 20 mM phosphate buffer (pH 7.0) containing 10% casein, and the resulting solution was stirred and then allowed to stand at 37° C. to effect the enzyme reaction. One hour thereafter, 12.5 μl of a solution containing 0.0188 unit of the protein-deamidating enzyme was added thereto, and the mixture was stirred and then allowed to stand at 37° C. A portion of the reaction solution was sampled after 1, 2, 4 or 24 hours of the reaction and subjected to SDS-polyacrylamide gel electrophoresis using 2 to 15% SDS-polyacrylamide gel. As a control, the same test was carried out using a sample obtained by adding water instead of the protein-deamidating enzyme solution.

Figure 16:
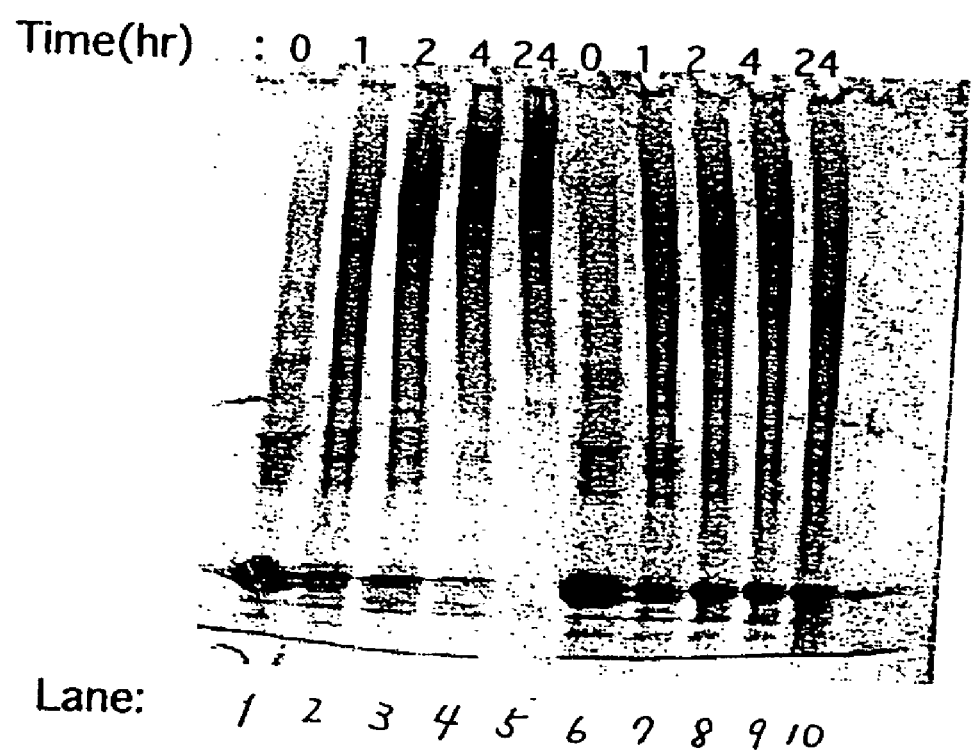
FIG. 16 is a photograph showing results of SDS-polyacrylamide gel electrophoresis in Example 23 in which protein-deamidating enzyme was added during the reaction by transglutaminase.

The results are shown in FIG. 16, and the samples applied to respective lanes in FIG. 16 are shown in Table 5.

TABLE 5

| Lane | Protein-deamidating enzyme | Time (h) |
|---|---|---|
| 1 | − | 0 |
| 2 | − | 1 |
| 3 | − | 2 |
| 4 | − | 4 |
| 5 | − | 24 |
| 6 | − | 0 |
| 7 | + | 1 |
| 8 | + | 2 |
| 9 | + | 4 |
| 10 | + | 24 |

As in evident from the results shown in FIG. 16, in the control reaction in which the protein-deamidating enzyme was not added, molecular weight of the protein increases with the lapse of time by its cross-linking reaction and the band of casein monomer observed at 0 hour decreases and disappears, while the pattern at the time of the addition of the protein-deamidating enzyme (lane 7) does not change with the lapse of time in the reaction in which the enzyme was added. This means that the cross-link polymerization reaction of transglutaminase was stopped by the addition of the protein-deamidating enzyme.

A solution (12.5 μl) containing 0.0125 units of transglutaminase derived from *Streptoverticillium* was added to 25 μl of 20 mM phosphate buffer (pH 7.0) containing 10% deamidated casein obtained in Example 18, the mixture was stirred and then allowed to stand at 37° C. A portion of the reaction solution was sampled after 1, 2, 4 to 24 hours of the reaction and subjected to SDS-polyacrylamide gel electrophoresis using 2 to 15% SDS-polyacrylamide gel. As a control, the same test was using untreated casein instead of deamidated casein.

Figure 17:
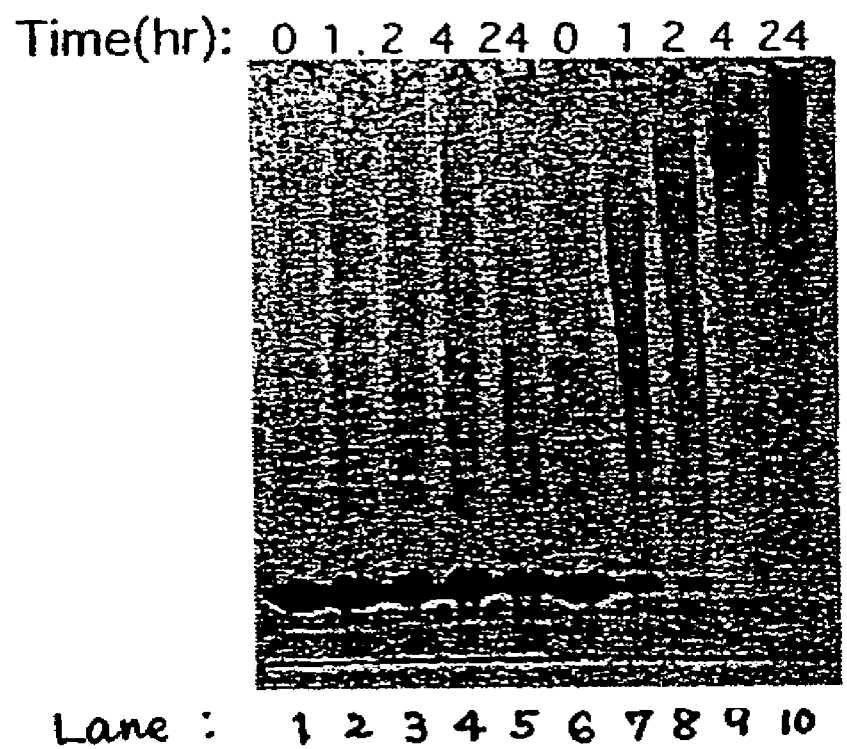
FIG. 17 is a photograph showing results of SDS-polyacrylamide gel electrophoresis of deamidated casein teated with transglutaminase in Example 23.

The results are shown in FIG. 17, and the samples applied to respective lanes in FIG. 17 are shown in Table 6.

TABLE 6

| Lane | Substrate protein | Time (h) |
|---|---|---|
| 1 | Deamidated casein | 0 |
| 2 | Deamidated casein | 1 |
| 3 | Deamidated casein | 2 |
| 4 | Deamidated casein | 4 |
| 5 | Deamidated casein | 24 |
| 6 | casein | 0 |
| 7 | casein | 1 |
| 8 | casein | 2 |
| 9 | casein | 4 |
| 10 | casein | 24 |

As is evident from the results shown in FIG. 17, in the control reaction in which the enzyme-untreated casein was used, molecular weight of the protein increases with the lapse of time by its cross-linking reaction and the band of casein monomer observed at 0 hour decreases and disappears, while the band observed at 0 hour in the reaction using deamidated casein (lane 1) does not change with the lapse of time in the reaction. This means that proteins deamidated by the protein-deamidating enzyme cannot be a substrate for the transglutaminase.

EXAMPLE 24

Production of Pudding-Like Food Using Transglutaminase and Protein-Deamidating Enzyme Commercially available milk was concentrated under a reduced pressure, 5 g of sugar was dissolved in the thus obtained concentrate and then the resulting solution was mixed with 1 unit of *Streptoverticillium* transglutaminase and incubated at 55° C. When appropriate gel was formed, the gel was mixed with 1.5 units of the protein-deamidating enzyme and stirred to stop the transglutaminase reaction and then cooled. As the results, it was able to produce a pudding-like food preparation having desirable softness.

EXAMPLE 25

Improvements in Functionality of Deamidated Casein (Solubility and Dispersibility)

Deamidated casein powder obtained in Example 18 and enzyme-untreated casein obtained in comparative experiment were measured for the solubility and dispersibility by the method similar to Example 12.

Figure 18:
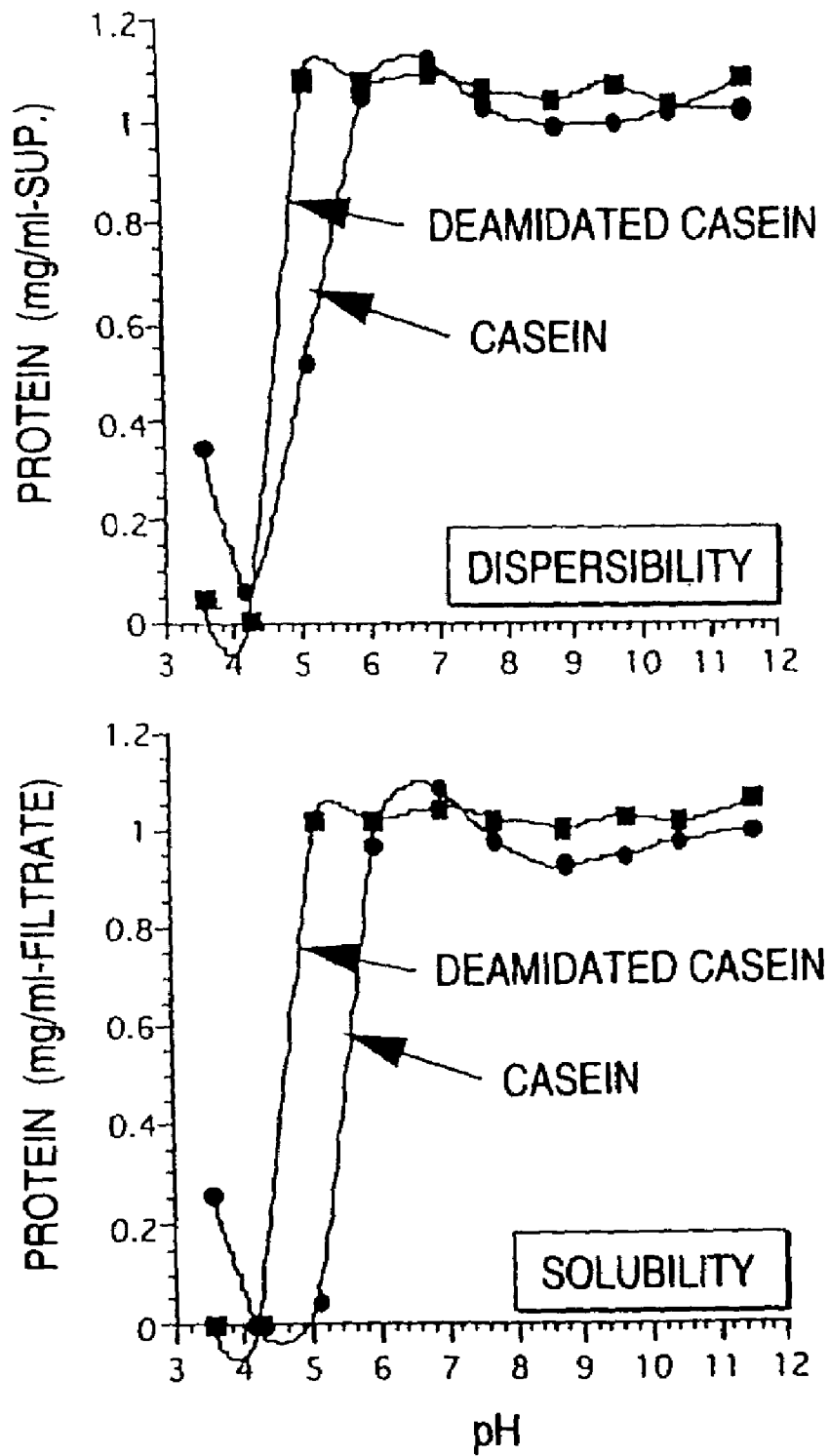
FIG. 18 is a photograph showing dispersibility and solubility of deamidated casein in Example 25, in which the closed square indicates results of casein treated with the protein-deamidating enzyme and the closed circle indicates results of untreated casein.

As shown in FIG. 18, deamidated casein showed extremely improved dispersibility and solubility in comparison with enzyme-untreated casein, expecially at the pH range of usual foods (i.e., from about pH 4 to about pH 5).

The following examples are provided to further illustrate the present invention. Unless otherwise noted, the gene manipulation techniques were carried out in accordance with the methods described in the literatures (for example, "*Molecular Cloning*" 2nd ed., Cold Spring Harbor Laboratory Press, 1989).

EXAMPLE 26

Isolation of Gene Coding for *Chryseobacterium gleum* JCM 2410 Protein-Deamidating Enzyme a) Isolation of Chromosomal DNA A 3.3 ml of chromosomal DNA solution having a concentration of 190 µg/ml was obtained from 100 ml of culture in accordance with the method described in "*Current Protocols in Molecular Biology*", Unit 2.4 (John Wiley & Sons, Inc., 1994).

b) Determination of Partial Amino Acid Sequence

The purified protein-deamidating enzyme obtained in Example 9 was applied to a protein sequenser (manufactured by Applied Biosystems) to determine an N-terminal amino acid sequence of 20 residues shown in the Sequence No. 1. Next, the purified protein-deamidating enzyme obtained in Example 9 was reduced and alkylated using performic acid and then hydrolyzed with trypsin. The thus obtained hydrolysate was applied to a reverse phase liquid chromatography, and one of the separated peptide fractions was applied to the protein sequenser to determine an internal amino acid sequence of 20 residues shown in the Sequence No. 2.

```
Sequence No. 1:
Ala-Val-Ser-Val-Ile-Pro-Asp-Leu-Ala-Thr-Leu-Asn-
Ser-Leu-Phe-Thr-Gln-Ile-Lys-Asn Sequence No. 2:
Ser-Pro-Ser-Gly-Ser-Leu-Leu-Tyr-Asp-Asn-Asn-Tyr-
Val-Asn-Thr-Asn-Cys-Val-Leu-Asn
``` c) Preparation of DNA Probe by PCR

Based on the N-terminal region amino acid sequence and the internal amino acid sequence, the following two mixed oligonucleotides were synthesized using a DNA synthesizer (manufactured by Applied Biosystems) and used as PCR primers.

```
Sequence No. 3
Sense primer:
5'-(TA) (CG) IGTIAT (TCA) CCIGA (TC) (CT) T (TCAG) AC-3'

Sequence No. 4
Antisense primer:
5'-A (AG) (TCAG) AC (AG) CA (AG) TT (TCAG) GT (AG) TT (TCAG) AC-3'
```

Using these primers and the *Chryseobacterium gleum* JCM 2410 chromosomal DNA as the template, PCR reaction was carried out using Omnigene Thermal Cycler (manufactured by Hybaid) under the following conditions.

<PCR Reaction Solution>

| | |
|---|---|
| 10 × PCR reaction buffer (manufactured by Perkin Elmer) | 5.0 µl |
| dNTP mixture solution (each 2.5 mM, manufactured by Promega) | 4.0 µl |
| 20 µM sense primer | 10.0 µl |
| 20 µM antisense primer | 10.0 µl |
| distilled water | 20.25 µl |
| chromosomal DNA solution (190 µg/ml) | 0.5 µl |
| Taq DNA polymerase (manufactured by Perkin Elmer) | 0.25 µl |

<PCR Reaction Condition>

| | | |
|---|---|---|
| Stage 1: | denaturation (94° C., 5 minutes) | 1 cycle |
| Stage 2: | denaturation (94° C., 1 minute) annealing (44° C., 1 minute) elongation (72° C., 1 minute) | 30 cycles |
| Stage 3: | elongation (72° C., 10 minutes) | 1 cycle |

When the thus obtained DNA fragment of about 0.48 kb was cloned into pCRII (manufactured by Invitrogene) and then its nucleotide sequence was determined, a nucleotide sequence coding for the aforementioned partial amino acid sequence was found in a region just after the sense primer and just before the antisense primer. This DNA fragment was used as a DNA probe for use in the cloning of the complete gene.

d) Preparation of Gene Library

As a result of the Southern hybridization analysis of the *Chryseobacterium gleum* JCM 2410 chromosomal DNA, a single band of about 3.7 kb capable of hybridizing with the probe DNA was found in an EcoRI digest. In order to carry out cloning of this EcoRI DNA fragment of about 3.7 kb, a gene library was prepared in the following manner. The chromosomal DNA prepared in the aforementioned step a) was digested with EcoRI, and the thus obtained digest was ligated to an EcoRI-treated λ ZAPII (manufactured by Stratagene) and packaged using Gigapack III Gold (manufactured by Stratagene) to obtain the gene library.

e) Screening of Gene Library

The 0.48 kb DNA fragment obtained in the aforementioned step c) was labeled using Megaprime DNA Labeling System (manufactured by Amersham) and $^{32}P$-α-dCTP. Using this as a DNA probe, the gene library obtained in the above step d) was screened by plaque hybridization. Phage particles were recovered from the thus obtained positive plaques, and then a plasmid p7T-1 containing an EcoRI fragment of about 3.7 kb was obtained by the in vivo excision method in accordance with the instruction provided by Stratagene.

f) Determination of Nucleotide Sequence

Nucleotide sequence of the plasmid p7T-1 was determined in the conventional way. The nucleotide sequence which encodes the protein-deamidating enzyme is shown in Sequence No. 5. Also, amino acid sequence encoded by the Sequence No. 5 is shown in Sequence No. 6. The N-terminal region amino acid sequence (Sequence No. 1) and internal amino acid sequence (Sequence No. 2) determined in the aforementioned step b) were found in this amino acid sequence.

```
Sequence No. 5
GCAGTCAGTGTTATTCCTGATCTGGCAACGCTGAACAGTTTATTTACCCA

GATCAAAAACCAGGCTTGCGGAACTTCTACAGCATCTTCTCCTTGTATCA

CCTTCAGATATCCGGTTGACGGATGTTATGCAAGGGCTCACAAAATGAGA

CAAATCCTATTGAACGCCGGCTATGACTGTGAAAAGCAGTTCGTATATGG

TAATCTGAGAGCTTCTACAGGAACATGCTGTGTATCATGGGTATATCACG

TAGCAATTTTGGTAAGCTTCAAAAATGCTTCAGGAATTGTTGAAAAAAGA

ATCATAGATCCTTCATTATTCTCCAGCGGTCCTGTAACAGATTCTGCATG

GAGAGCTGCATGTACCAACACAAGCTGCGGATCTGCGTCTGTATCTTCCT

ACGCCAATACAGCAGGAAATGTTTACTACAGAAGTCCGTCAGGTTCATTA

CTGTATGATAACAACTATGTGAATACCAATTGTGTATTAAACATATTCTC

ATCCCTTTCAGGATGTTCTCCTTCCCCAGCACCAAGTGTAGCAAGCTGTG

GATTT (555 bp)

Sequence No. 6
AVSVIPDLATLNSLFTQIKN

QACGTSTASSPCITFRYPVD

GCYARAHKMRQILLNAGYDC

EKQFVYGNLRASTGTCCVSW

VYHVAILVSFKNASGIVEKR

IIDPSLFSSGPVTDSAWRAA

CTNTSCGSASVSSYANTAGN

VYYRSPSGSLLYDNNYVNTN

CVLNIFSSLSGCSPSPAPSV

ASCGF (185 amino acids)
```

The open leading frame of this gene is shown in Sequence No. 11 below. A prepro protein having 319 amino acid residues as shown in Sequence No. 12 below are encoded by the gene, in which N-terminal 134 amino acid residues (underlined in Sequence No. 11) correspond to the prepro region and the remaining 185 amino acid residues correspond to the mature protein (cf. Sequence No. 6). Among the 134 residues of the prepro region, the N-terminal 21 residues have the characteristics of the signal sequence. Accordingly, it is considered that the N-terminal 21 residues correspond to the pre region and remaining 113 residues correspond to the pro region.

The present invention is not particularly limited to polypeptides having protein-deamidating activity and nucleotides encoding the same, but also includes the longer polypeptides comprising the polypeptides having protein-deamidating activity (e.g., prepro proteins, pro proteins, and the like) and nucleotides encoding the same.

```
Sequence No. 11
   AATAAGTGAACTATTACAATTAAAAAGTTCACTAAAACTAAACACCAAAATATAAAAACT

ATGAAAAAATTTCTGTTATCCATGATGGCATTCGTGACGATTCTGTCATTCAATGCCTGC

1 M K K F L L S M M A F V T I L S F N A C                          20

TCAGATTCAAGTGCCAACCAGGACCCGAATCTTGTCGCTAAAGAATCTAACGAAGTCGCT

21 S D S S A N Q D P N L V A K E S N E V A                          40

ATGAAAGATTTCGGTAAGACTGTTCCGGTAGGGATTGAAAAAGAAGATGGAAAATTTAAA

41 M K D F G K T V P V G I E K E D G K F K                          60

ATCTCATTTATGGTTACTGCCCAGCCGTATGAAATTGCGGACAGTAAAGAAAATGCAGGT
```

-continued

61 I S F M V T Q P Y E I A D S K E N A G             80
TATATTTCCATGATCAGACAGGCTGTTGAGAATGAAACTCCCGTTCATGTTTTCCTTAAA

81 Y I S M I R Q A V E N E T P V H V F L K           100
GTCAACACCAATAAAATTGCAAAAGTAGAAAAAGCAACAGATGATGACATCCGTTATTTT

101 V N T N K I A K V E K A T D D D I R Y F          120
AAATCTGTATTCAACAAGCAAGAGAGAGGTGAAAGCAACAAAGCAGTCAGTGTTATTCCT

121 K S V F N K Q E RG E S N K A V S V I P           140
GATCTGGCAACGCTGAACAGTTTATTTACCCAGATCAAAAACCAGGCTTGCGGAACTTCT

141 D L A T L N S L F T Q I K N Q A C G T S          160
ACAGCATCTTCTCCTTGTATCACCTTCAGATATCCGGTTGACGGATGTTATGCAAGGGCT

161 T A S S P C I T F R Y P V D G C Y A R A          180
CACAAAATGAGACAAATCCTATTGAACGCCGGCTATGACTGTGAAAAGCAGTTCGTATAT

181 H K M R Q I L L N A G Y D C E K Q F V Y          200
GGTAATCTGAGAGCTTCTACAGGAACATGCTGTGTATCATGGGTATATCACGTAGCAATT
201 G N L R A S T G T C C V S W V Y H V A I          220
TTGGTAAGCTTCAAAAATGCTTCAGGAATTGTTGAAAAAAGAATCATAGATCCTTCATTA

221 L V S F K N A S G I V E K R I I D P S L          240
TTCTCCAGCGGTCCTGTAACAGATTCTGCATGGAGAGCTGCATGTACCAACACAAGCTGC

241 F S S G P V T D S A W R A A C T N T S C          260
GGATCTGCGTCTGTATCTTCCTACGCCAATACAGCAGGAAATGTTTACTACAGAAGTCCG

261 G S A S V S S Y A N T A G N V Y Y R S P          280
TCAGGTTCATTACTGTATGATAACAACTATGTGAATACCAATTGTGTATTAAACATATTC

281 S G S L L Y D N N Y V N T N C V L N I F          300
TCATCCCTTTCAGGATGTTCTCCTTCCCCAGCACCAAGTGTAGCAAGCTGTGGATTTTAA

301 S S L S G C S P S P A P S V A S C G F *          319
TTTTGATACATTGCAGGAGCTTTTTATTTAATACTTTTTATTATGAAAGCCTGGTCCTAT  (1080)

Sequence No. 12
M K K F L L S M M A F V T I L S F N A C

S D S S A N Q D P N L V A K E S N E V A

M K D F G K T V P V G I E K E D G K F K

I S F M V T A Q P Y E I A D S K E N A G

Y I S M I R Q A V E N E T P V H V F L K

V N T N K I A K V E K A T D D D I R Y F

K S V F N K Q E R G E S N K A V S V I P

D L A T L N S L F T Q I K N Q A C G T S

T A S S P C I T F R Y P V D G C Y A R A

H K M R Q I L L N A G Y D C E K Q F V Y

G N L R A S T G T C C V S W V Y H V A I

L V S F K N A S G I V E K R I I D P S L

F S S G P V T D S A W R A A C T N T S C

G S A S V S S Y A N T A G N V Y Y R S P

```
SGSLLYDNNYVNTNCVLNIF

SSLSGCSPSPAPSVASCGF
```

EXAMPLE 27

Production of Protein-Deamidating Enzyme in *Escherichia coli* a) Construction of Plasmid for Use in the Expression of Protein-Deamidating Enzyme in *Escherichia coli*

Based on the DNA sequences which encode the N-terminal region amino acid sequence and the C-terminal region amino acid sequence, the following two oligonucleotides were synthesized using a DNA synthesizer (manufactured by Applied Biosystems) and used as PCR primers.

```
Sequence No. 7
Sense primer:
5'-GCGAATTCGCAGTCAGTGTTATTCCTGATC-3'

Sequence No. 8
Antisense primer:
5'-TAGAATTCTTAAAATCCACAGCTTGCTAC-3'
```

Using these primers and the protein-deamidating enzyme gene-containing plasmid p7T-1 as the template, PCR reaction was carried out using Omnigene Thermal Cycler (manufactured by Hybaid) under the following conditions.

<PCR Reaction Solution>

| | |
|---|---|
| 10 × PCR reaction buffer (manufactured by Perkin Elmer) | 10.0 μl |
| dNTP mixture solution (each 2.5 mN, manufactured by Promega) | 8.0 μl |
| 20 μM sense primer | 2.5 μl |
| 20 μM antisense primer | 2.5 μl |
| distilled water | 75.5 μl |
| plasmid p7T-1 solution (50 μg/ml) | 1.0 μl |
| Taq DNA polymerase (manufactured by Perkin Elmer) | 0.5 μl |

<PCR Reaction Condition>

| | | |
|---|---|---|
| Stage 1: | denaturation (94° C., 5 minutes) | 1 cycle |
| Stage 2: | denaturation (94° C., 1 minute) | 30 cycles |
| | annealing (55° C., 1 minute) | |
| | elongation (72° C., 1 minute) | |
| Stage 3: | elongation (72° C., 10 minutes) | 1 cycle |

The thus obtained DNA fragment of about 0.57 kb was cloned into pCRII (manufactured by Invitrogene) to confirm that the nucleotide sequence was correct, and then the DNA fragment of about 0.57 kb was recovered from the plasmid by EcoRI treatment. This DNA fragment was inserted into an expression vector pGEX-1λT for *E. coli* use (manufactured by Pharmacia), and the protein-deamidating enzyme-encoding DNA was connected to the C-terminal-corresponding side of the glutathione S transferase-encoding DNA contained in the pGEX-1λT, in the same direction. The thus obtained plasmid pN7-7 for use in the expression of protein-deamidating enzyme in *E. coli* can express a fusion protein of glutathione S transferase with protein-deamidating enzyme under control of tac promoter, and the protein-deamidating enzyme can be cut off from the fusion protein by thrombin treatment.

b) Expression of Protein-Deamidating Enzyme in *E. coli*

A transformant was obtained by introducing the expression plasmid pN7-7 into *E. coli* BL21 (manufactured by Pharmacia). As a control, a transformant of *E. coli* BL21 having the expression vector pGEX-1λT was also obtained. Each of these transformants was cultured at 37° C. on a 200 rpm rotary shaker using LB medium containing 100 μg/ml of ampicillin, and the cells obtained at the logarithmic growth phase ($OD_{600}$=0.9-1.0) were mixed with 0.1 mM in final concentration of IPTG, cultured for 4 hours under the same conditions and then collected. The thus collected cells were suspended in 1/10 volume culture broth of 50 mM Tris-HCl (pH 8.0)/2 mM MEDTAL mixed with 0.1 mg/ml in final concentration of egg white lysozyme and 0.1% in final concentration of Triton X-100 and allowed to stand at 30° C. for 15 minutes, and then the thus formed viscous DNA was sheared by mild ultrasonic treatment (3 cycles of 10 sec. on and 30 sec. off) to obtain a cell extract. A 100 μl portion of the cell extract was mixed with 4 μl of thrombin (1 U/μl in 9 mM sodium phosphate (pH 6.5)/140 mM NaCl) and allowed to stand at room temperature for 16 hours to obtain thrombin-treated cell extract. A sample obtained by adding 4 μl of a buffer solution (9 mM sodium phosphate (pH 6.5)/140 mM NaCl) and carrying out the same reaction was used as a control of the thrombin treatment.

The protein-deamidating enzyme activity of the thus obtained samples were measured, with the results shown in the following table.

TABLE 7

| | | | Protein deamidation activity (mU/ml) | |
|---|---|---|---|---|
| Sample | Transformant | Thrombin treatment | Substrate: Z-Gln-Gly | Substrate: casein |
| 1 | *E. coli* BL21/pN7-7 | − | 30.02 | 16.10 |
| 2 | *E. coli* BL21/pN7-7 | + | 35.36 | 19.99 |
| 3 | *E. coli* BL21/pGEX-1λT | − | 0.00 | 0.00 |
| 4 | *E. coli* BL21/pGEX-1λT | + | 0.00 | 0.00 |

Thus, it is apparent that the *E. coli* strain having the protein-deamidating enzyme expression plasmid pN7-7 expresses the protein deamidation activity. On the contrary, expression of the protein deamidation activity was not found in the control *E. coli* strain having the expression vector pGEX-1λT. Separately from this, each of these samples was subjected to 12% SDS-polyacrylamide gel electrophoresis to carry out Western blotting analysis using an antibody specific for the protein-deamidating enzyme. As a result, a band which reacted with the antibody was detected in the sample 1 at a position of about 43 kDa in molecular weight which seemed to be a fusion protein of glutathione S transferase with the protein-deamidating enzyme, and a band was detected in the sample 2 at a position of about 20 kDa in molecular weight corresponding to the protein-deamidating enzyme, in addition to the band of about 43 kDa in molecular weight. On the other hand, a band capable of reacting with the antibody was not detected in the samples 3 and 4. On the basis of these results, it was confirmed that a recombinant protein-deamidating enzyme can be produced in *E. coil* using the protein-deamidating enzyme gene obtained by the present invention.

EXAMPLE 28

Expression of Protein-Deamidating Enzyme in Filamentous Fungi a) Construction of Expression Cassette for Protein-Deamidating Enzyme in Filamentous Fungi Based on the DNA sequences which encode the N-terminal region amino acid sequence and the C-terminal region amino acid sequence, the following two oligonucleotides were synthesized using a DNA synthesizer (manufactured by Applied Biosystems) and used as PCR primers.

```
Sequence No. 9
Sense primer:
5'-GCGTCGACGCAGTCAGTGTTATTCCTGATC-3'

Sequence No. 10
Antisense primer:
5'-TAGGATCCTTAAAATCCACAGCTTGCTAC-3'
```

Using these primers and the protein-deamidating enzyme gene-containing plasmid p7T-1 as the template, PCR reaction was carried out in the same manner as described in Example 27. The thus obtained DNA fragment of about 0.57 kb was cloned into pCRII (manufactured by Invitrogene) to confirm that the nucleotide sequence was correct, and then the DNA fragment of about 0.57 kb was recovered from the plasmid by SalI/BamHI treatment. This DNA fragment was inserted into the SalI/BamHI site of a filamentous fungi expression cassette construction vector pY4' (JP-A-123987) to obtain a plasmid pD5'. This plasmid contains a DNA sequence which encodes a fusion protein composed of mono and diacylglycerol lipases originated from *Penicillium camembertii* and the protein-deamidating enzyme. An unnecessary nucleotide sequence existing in the connecting part of the mono and diacylglycerol lipases and protein-deamidating enzyme (5'-GTCGAC-3', this sequence corresponds to the SalI site introduced to connect the protein-deamidating enzyme gene) of this plasmid was deleted by site-specific mutation to obtain a plasmid pD5. This plasmid contains a DNA sequence which encodes a fusion protein in which the protein-deamidating enzyme is connected to just after the processing sites of C-terminal regions of the mono and diacylglycerol lipases (Lys-Arg sequences, 3rd and 2nd positions from the C-terminal, respectively). This fusion protein is expressed in filamentous fungi and yeast under control of the promoter and terminator of the *Penicillium camembertii* mono and diacylglycerol lipase genes, which are present in its upstream and downstream regions. Also, the protein-deamidating enzyme can be cut off from the thus expressed fusion protein through its digestion at the Lys-Arg site by a protease of the host (JP-A-7-123987).

b) Expression of Protein-Deamidating Enzyme in *Penicillium camembertii*

The plasmid pD5 obtained in the above step a) was introduced into *Penicillium camembertii* U-150 by co-transformation together with a *Penicillium camembertli* transformation plasmid pH1. As a control, a transformant was obtained using pH1 alone. When the thus obtained transformants were cultured and the protein-deamidating enzyme activity in the culture filtrates was measured, production of 10.3 mU/ml (substrate, Z-Gln-Gly) of the protein-deamidating enzyme was found in the transformant transformed with the plasmid pD5. On the other hand, the activity was not detected in the culture filtrate of the transformant transformed with plasmid pH1 alone. In this connection, the plasmid pH1 and its transformation method are described in detail in JP-A-7-123987.

EXAMPLE 29

Expression of Protein-Deamidating Enzyme in *Aspergillus oryzae*

The plasmid pD5 obtained in the step a) of Example 28 was introduced into *Aspergillus oryzae* AO1.1 (*Mol. Gen. Genet.*, 218, 99-104, 1989) by co-transformation together with an *Aspergillus oryzae* transformation plasmid pN3. As a control, a transformant was obtained using pN3 alone. When the thus obtained transformants were cultured and the protein-deamidating enzyme activity in the culture filtrates was measured, production of 4.51 mU/ml (substrate, Z-Gln-Gly) of the protein-deamidating enzyme was found in the transformant transformed with the plasmid pD5. On the other hand, the activity was not detected in the culture filtrate of the transformant transformed with plasmid pN3 alone. In this connection, the plasmid pN3 and its transformation method are described in detail in JP-A-7-123987.

It was confirmed based on the results of Examples 28 and 29 that a recombinant protein-deamidating enzyme can be produced by filamentous fungi utilizing the protein-deamidating enzyme gene obtained by the present invention.

A novel enzyme capable of acting upon glutamine in protein and thereby catalyzing the deamidation reaction was found for the first time in microorganisms, and a broad range of applications are expected by this enzyme.

Also, since the primary structure and gene structure of the protein-deamidating enzyme were provided by the present invention, inexpensive and high purity production of polypeptide having protein-deamidating enzyme activity by gene engineering techniques became possible.

While the invention has been described in detail and with reference to specific embodiments thereof, it will be apparent to one skilled in the art that various changes and modifications can be made therein without departing from the spirit and scope thereof.

This application is based on Japanese patent application No. Hei. 10-173940, filed on Jun. 4, 1998, and incorporated herein by reference.

What is claimed is:

1. A method for modifying a target protein or peptide with a molecular weight of 5,000 or more, comprising allowing an enzyme, which is capable of deamidating amido groups in target proteins and peptides by directly acting upon said amido groups, without cutting peptide bonds and without cross-linking said target proteins or peptides, to act on said target protein or peptide, wherein said enzyme is selected from the group consisting of (a) a polypeptide which comprises the amino acid sequence set forth in SEQ ID NO:6, (b) a polypeptide which comprises the amino acid sequence encoded by the nucleotide sequence set forth in SEQ ID NO:5, and (c) a polypeptide which comprises the amino acid sequence encoded by the nucleotide sequence which has a homology of 80% or more with the nucleotide sequence set forth in SEQ ID NO:5.

2. The method of claim 1, wherein said target protein or peptide to be modified is derived from a plant or animal such that the solubility, dispersibility, foamability, foam stability, emulsification ability, and emulsification stability of said protein or peptide is improved in comparison to that of the protein or peptide untreated with said enzyme.

3. The method of claim 1, wherein said target protein or peptide to be modified is derived from food such that the solubility, dispersibility, foamability, foam stability, emulsification ability, and emulsification stability of said food is improved in comparison to that of the food untreated with said enzyme.

4. The method of claim 1, wherein said target protein or peptide is contained in a crude material such that the extraction efficiency of said target protein or peptide is improved in comparison to that of the protein or peptide untreated with said enzyme.

5. A method for controlling a transglutaminase reaction, which comprises using an enzyme having an activity to deamidate amido groups in target protein and peptide by directly acting upon the groups without causing severing of peptide bond and cross-linking of protein, wherein said enzyme is selected from the group consisting of (a) a polypeptide which comprises the ammo acid sequence set forth in SEQ ID NO:6, (b) a polypeptide which comprises the amino acid sequence encoded by the nucleotide sequence set forth in SEQ ID NO:5 and (c) a polypeptide which comprises the amino acid sequence encoded by the nucleotide sequence which has a homology of 80% or more with the nucleotide sequence set forth in SEQ ID NO:5 and said target protein or peptide has a molecular weight of 5,000 or more.

6. The method of claim 5, wherein said enzyme is allowed to act on said target protein or peptide before said transglutaminase is allowed to act on said target protein or peptide.

7. The method of claim 5, wherein said transglutaminase is allowed to act on the target protein or peptide before said enzyme is allowed to act on said target protein or peptide.

8. The method of claim 5, wherein said enzyme and said transglutaminase are allowed to act on said target protein or peptide at the same time.

9. The method of claim 1, which further comprises the step of allowing a protease and a glutaminase to act on said target protein or peptide.

* * * * *

SEQUENCE LISTING

<160> NUMBER OF SEQ ID NOS: 12

<210> SEQ ID NO 1
<211> LENGTH: 20
<212> TYPE: PRT
<213> ORGANISM: Chryseobacterium gleum

<400> SEQUENCE: 1

Ala Val Ser Val Ile Pro Asp Leu Ala Thr Leu Asn Ser Leu Phe Thr
 1               5                  10                  15

Gln Ile Lys Asn
            20

<210> SEQ ID NO 2
<211> LENGTH: 20
<212> TYPE: PRT
<213> ORGANISM: Chryseobacterium gleum

<400> SEQUENCE: 2

Ser Pro Ser Gly Ser Leu Leu Tyr Asp Asn Asn Tyr Val Asn Thr Asn
 1               5                  10                  15

Cys Val Leu Asn
            20

<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: modified_base
<222> LOCATION: (3)
<223> OTHER INFORMATION: i
<220> FEATURE:
<221> NAME/KEY: modified_base
<222> LOCATION: (6)
<223> OTHER INFORMATION: i
<220> FEATURE:
<221> NAME/KEY: modified_base
<222> LOCATION: (12)
<223> OTHER INFORMATION: i
<220> FEATURE:
<221> NAME/KEY: modified_base
<222> LOCATION: (18)
<223> OTHER INFORMATION: A, T, C or G

<400> SEQUENCE: 3
wsngtnathc cngayytnac                                              20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: modified_base
<222> LOCATION: (3)
<223> OTHER INFORMATION: A, T, C or G
<220> FEATURE:
<221> NAME/KEY: modified_base
<222> LOCATION: (12)
<223> OTHER INFORMATION: A, T, C or G

```
<220> FEATURE:
<221> NAME/KEY: modified_base
<222> LOCATION: (18)
<223> OTHER INFORMATION: A, T, C or G

<400> SEQUENCE: 4
arnacrcart tngtrttnac                                                    20

<210> SEQ ID NO 5
<211> LENGTH: 555
<212> TYPE: DNA
<213> ORGANISM: Chryseobacterium gleum

<400> SEQUENCE: 5
gcagtcagtg ttattcctga tctggcaacg ctgaacagtt tatttaccca gatcaaaaac        60
caggcttgcg gaacttctac agcatcttct ccttgtatca ccttcagata tccggttgac       120
ggatgttatg caagggctca caaaatgaga caaatcctat tgaacgccgg ctatgactgt       180
gaaaagcagt tcgtatatgg taatctgaga gcttctacag aacatgctg tgtatcatgg        240 gtatatcacg tagcaatttt ggtaagcttc aaaaatgctt caggaattgt tgaaaaaga       300 atcatagatc cttcattatt ctccagcggt cctgtaacag attctgcatg gagagctgca      360
tgtaccaaca caagctgcgg atctgcgtct gtatcttcct acgccaatac agcaggaaat      420
gtttactaca gaagtccgtc aggttcatta ctgtatgata caactatgt gaataccaat       480 tgtgtattaa acatattctc atcccttcca ggatgttctc cttccccagc accaagtgta      540
gcaagctgtg gattt                                                       555

<210> SEQ ID NO 6
<211> LENGTH: 185
<212> TYPE: PRT
<213> ORGANISM: Chryseobacterium gleum

<400> SEQUENCE: 6

Ala Val Ser Val Ile Pro Asp Leu Ala Thr Leu Asn Ser Leu Phe Thr
  1               5                  10                  15

Gln Ile Lys Asn Gln Ala Cys Gly Thr Ser Thr Ala Ser Ser Pro Cys
             20                  25                  30

Ile Thr Phe Arg Tyr Pro Val Asp Gly Cys Tyr Ala Arg Ala His Lys
         35                  40                  45

Met Arg Gln Ile Leu Leu Asn Ala Gly Tyr Asp Cys Glu Lys Gln Phe
     50                  55                  60

Val Tyr Gly Asn Leu Arg Ala Ser Thr Gly Thr Cys Cys Val Ser Trp
 65                  70                  75                  80

Val Tyr His Val Ala Ile Leu Val Ser Phe Lys Asn Ala Ser Gly Ile
                 85                  90                  95

Val Glu Lys Arg Ile Ile Asp Pro Ser Leu Phe Ser Ser Gly Pro Val
            100                 105                 110

Thr Asp Ser Ala Trp Arg Ala Ala Cys Thr Asn Thr Ser Cys Gly Ser
        115                 120                 125

Ala Ser Val Ser Ser Tyr Ala Asn Thr Ala Gly Asn Val Tyr Tyr Arg
    130                 135                 140

Ser Pro Ser Gly Ser Leu Leu Tyr Asp Asn Asn Tyr Val Asn Thr Asn
145                 150                 155                 160
```

Cys Val Leu Asn Ile Phe Ser Ser Leu Ser Gly Cys Ser Pro Ser Pro
                165                 170                 175

Ala Pro Ser Val Ala Ser Cys Gly Phe
            180                 185

<210> SEQ ID NO 7
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
gcgaattcgc agtcagtgtt attcctgatc                                      30

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
tagaattctt aaaatccaca gcttgctac                                       29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
gcgtcgacgc agtcagtgtt attcctgatc                                      30

<210> SEQ ID NO 10
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 10
taggatcctt aaaatccaca gcttgctac                                       29

<210> SEQ ID NO 11
<211> LENGTH: 1080
<212> TYPE: DNA
<213> ORGANISM: Chryseobacterium gleum
<220> FEATURE:
<221> NAME/KEY: sig_peptide
<222> LOCATION: (61)..(462)
<220> FEATURE:
<221> NAME/KEY: mat_peptide
<222> LOCATION: (463)..(1017)
<220> FEATURE:
<221> NAME/KEY: CDS
<222> LOCATION: (61)..(1017)

<400> SEQUENCE: 11

```
aataagtgaa ctattacaat taaaaagttc actaaaacta aacaccaaaa tataaaaact      60 atg aaa aaa ttt ctg tta tcc atg atg gca ttc gtg acg att ctg tca      108
Met Lys Lys Phe Leu Leu Ser Met Met Ala Phe Val Thr Ile Leu Ser
         -130                -125                -120 ttc aat gcc tgc tca gat tca agt gcc aac cag gac ccg aat ctt gtc      156
Phe Asn Ala Cys Ser Asp Ser Ser Ala Asn Gln Asp Pro Asn Leu Val
        -115                -110                -105 gct aaa gaa tct aac gaa gtc gct atg aaa gat ttc ggt aag act gtt      204
Ala Lys Glu Ser Asn Glu Val Ala Met Lys Asp Phe Gly Lys Thr Val
        -100                 -95                 -90 ccg gta ggg att gaa aaa gaa gat gga aaa ttt aaa atc tca ttt atg      252
Pro Val Gly Ile Glu Lys Glu Asp Gly Lys Phe Lys Ile Ser Phe Met
     -85                 -80                 -75 gtt act gcc cag ccg tat gaa att gcg gac agt aaa gaa aat gca ggt      300
Val Thr Ala Gln Pro Tyr Glu Ile Ala Asp Ser Lys Glu Asn Ala Gly
-70                 -65                 -60                 -55 tat att tcc atg atc aga cag gct gtt gag aat gaa act ccc gtt cat      348
Tyr Ile Ser Met Ile Arg Gln Ala Val Glu Asn Glu Thr Pro Val His
                 -50                 -45                 -40 gtt ttc ctt aaa gtc aac acc aat aaa att gca aaa gta gaa aaa gca      396
Val Phe Leu Lys Val Asn Thr Asn Lys Ile Ala Lys Val Glu Lys Ala
            -35                 -30                 -25 aca gat gat gac atc cgt tat ttt aaa tct gta ttc aac aag caa gag      444
Thr Asp Asp Asp Ile Arg Tyr Phe Lys Ser Val Phe Asn Lys Gln Glu
        -20                 -15                 -10 aga ggt gaa agc aac aaa gca gtc agt gtt att cct gat ctg gca acg      492
Arg Gly Glu Ser Asn Lys Ala Val Ser Val Ile Pro Asp Leu Ala Thr
     -5                  -1   1                   5                  10 ctg aac agt tta ttt acc cag atc aaa aac cag gct tgc gga act tct      540
Leu Asn Ser Leu Phe Thr Gln Ile Lys Asn Gln Ala Cys Gly Thr Ser
                 15                  20                  25 aca gca tct tct cct tgt atc acc ttc aga tat ccg gtt gac gga tgt      588
Thr Ala Ser Ser Pro Cys Ile Thr Phe Arg Tyr Pro Val Asp Gly Cys
             30                  35                  40 tat gca agg gct cac aaa atg aga caa atc cta ttg aac gcc ggc tat      636
Tyr Ala Arg Ala His Lys Met Arg Gln Ile Leu Leu Asn Ala Gly Tyr
         45                  50                  55 gac tgt gaa aag cag ttc gta tat ggt aat ctg aga gct tct aca gga      684
Asp Cys Glu Lys Gln Phe Val Tyr Gly Asn Leu Arg Ala Ser Thr Gly
     60                  65                  70 aca tgc tgt gta tca tgg gta tat cac gta gca att ttg gta agc ttc      732
Thr Cys Cys Val Ser Trp Val Tyr His Val Ala Ile Leu Val Ser Phe
 75                  80                  85                  90 aaa aat gct tca gga att gtt gaa aaa aga atc ata gat cct tca tta      780
Lys Asn Ala Ser Gly Ile Val Glu Lys Arg Ile Ile Asp Pro Ser Leu
                 95                 100                 105 ttc tcc agc ggt cct gta aca gat tct gca tgg aga gct gca tgt acc      828
Phe Ser Ser Gly Pro Val Thr Asp Ser Ala Trp Arg Ala Ala Cys Thr
             110                 115                 120 aac aca agc tgc gga tct gcg tct gta tct tcc tac gcc aat aca gca      876
Asn Thr Ser Cys Gly Ser Ala Ser Val Ser Ser Tyr Ala Asn Thr Ala
         125                 130                 135 gga aat gtt tac tac aga agt ccg tca ggt tca tta ctg tat gat aac      924
Gly Asn Val Tyr Tyr Arg Ser Pro Ser Gly Ser Leu Leu Tyr Asp Asn
     140                 145                 150 aac tat gtg aat acc aat tgt gta tta aac ata ttc tca tcc ctt tca      972
Asn Tyr Val Asn Thr Asn Cys Val Leu Asn Ile Phe Ser Ser Leu Ser
155                 160                 165                 170
```

```
gga tgt tct cct tcc cca gca cca agt gta gca agc tgt gga ttt       1017
Gly Cys Ser Pro Ser Pro Ala Pro Ser Val Ala Ser Cys Gly Phe
            175                 180                 185 taattttgat acattgcagg agctttttat ttaatacttt ttattatgaa agcctggtcc  1077
tat                                                                1080

<210> SEQ ID NO 12
<211> LENGTH: 319
<212> TYPE: PRT
<213> ORGANISM: Chryseobacterium gleum

<400> SEQUENCE: 12

Met Lys Lys Phe Leu Leu Ser Met Met Ala Phe Val Thr Ile Leu Ser
            -130                -125                -120

Phe Asn Ala Cys Ser Asp Ser Ser Ala Asn Gln Asp Pro Asn Leu Val
            -115                -110                -105

Ala Lys Glu Ser Asn Glu Val Ala Met Lys Asp Phe Gly Lys Thr Val
        -100                -95                 -90

Pro Val Gly Ile Glu Lys Glu Asp Gly Lys Phe Lys Ile Ser Phe Met
        -85                 -80                 -75

Val Thr Ala Gln Pro Tyr Glu Ile Ala Asp Ser Lys Glu Asn Ala Gly
-70                 -65                 -60                 -55

Tyr Ile Ser Met Ile Arg Gln Ala Val Glu Asn Glu Thr Pro Val His
            -50                 -45                 -40

Val Phe Leu Lys Val Asn Thr Asn Lys Ile Ala Lys Val Glu Lys Ala
            -35                 -30                 -25

Thr Asp Asp Asp Ile Arg Tyr Phe Lys Ser Val Phe Asn Lys Gln Glu
        -20                 -15                 -10

Arg Gly Glu Ser Asn Lys Ala Val Ser Val Ile Pro Asp Leu Ala Thr
    -5                  -1  1                   5                  10

Leu Asn Ser Leu Phe Thr Gln Ile Lys Asn Gln Ala Cys Gly Thr Ser
                15                  20                  25

Thr Ala Ser Ser Pro Cys Ile Thr Phe Arg Tyr Pro Val Asp Gly Cys
                30                  35                  40

Tyr Ala Arg Ala His Lys Met Arg Gln Ile Leu Leu Asn Ala Gly Tyr
                45                  50                  55

Asp Cys Glu Lys Gln Phe Val Tyr Gly Asn Leu Arg Ala Ser Thr Gly
            60                  65                  70

Thr Cys Cys Val Ser Trp Val Tyr His Val Ala Ile Leu Val Ser Phe
75                  80                  85                  90

Lys Asn Ala Ser Gly Ile Val Glu Lys Arg Ile Ile Asp Pro Ser Leu
                95                  100                 105

Phe Ser Ser Gly Pro Val Thr Asp Ser Ala Trp Arg Ala Ala Cys Thr
            110                 115                 120

Asn Thr Ser Cys Gly Ser Ala Ser Val Ser Ser Tyr Ala Asn Thr Ala
            125                 130                 135

Gly Asn Val Tyr Tyr Arg Ser Pro Ser Gly Ser Leu Leu Tyr Asp Asn
        140                 145                 150

Asn Tyr Val Asn Thr Asn Cys Val Leu Asn Ile Phe Ser Ser Leu Ser
155                 160                 165                 170

Gly Cys Ser Pro Ser Pro Ala Pro Ser Val Ala Ser Cys Gly Phe
            175                 180                 185
```